United States Patent [19]

Vyas et al.

[11] Patent Number: 4,767,863

[45] Date of Patent: Aug. 30, 1988

[54] ISOXAZOLINE INTERMEDIATES

[75] Inventors: Dolatrai M. Vyas; Terrence W. Doyle, both of Fayetteville; Yulin Chiang, Clay, all of N.Y.

[73] Assignee: Bristol-Myers Company, New York, N.Y.

[21] Appl. No.: 66,289

[22] Filed: Jun. 25, 1987

Related U.S. Application Data

[60] Division of Ser. No. 737,752, May 28, 1985, which is a continuation of Ser. No. 368,180, Apr. 14, 1982, abandoned.

[51] Int. Cl.$^4$ .................. C07D 215/16; C07D 321/00; C07D 261/02; C07D 231/00
[52] U.S. Cl. .................................... 546/178; 549/347; 548/240; 548/110

[58] Field of Search ................ 549/347; 548/240, 110; 514/378; 546/178

[56] References Cited

U.S. PATENT DOCUMENTS 4,188,324  2/1980  Martin ................................. 548/240

Primary Examiner—Alan L. Rotman
Assistant Examiner—Robert C. Whittenbaugh
Attorney, Agent, or Firm—David M. Morse

[57] ABSTRACT

New and more efficient chemical processes are provided for preparing ($\alpha$S, 5S)-$\alpha$-amino-3-chloro-2-isoxazoline-5-acetic acid (AT-125), ($\alpha$S, 5S)-$\alpha$-amino-3-bromo-2-isoxazoline-5-acetic acid (bromo AT-125) and the C-5 epimers thereof. The disclosed processes allow the above-mentioned antitumor agents to be produced in high yield and purity with substantially fewer steps than prior art chemical procedures.

21 Claims, No Drawings

ISOXAZOLINE INTERMEDIATES

CROSS-REFERENCE TO RELATED APPLICATIONS

This application is a division of our co-pending application Ser. No. 737,752 filed May 28, 1985 which is a continuation of our application Ser. No. 368,180 filed Apr. 14, 1982, now abandoned.

BACKGROUND OF THE INVENTION

1. Field of the Invention

This invention relates to novel chemical processes for preparing (αS, 5S)-α-amino-3-chloro-2-isoxazoline-5-acetic acid (AT-125), (αS, 5S)-αamino-3-bromo-2-isoxazoline-5-acetic acid (bromo AT-125) and the C-5 epimers thereof. Also described are novel intermediates useful in said processes.

2. Description of the Prior Art

The heterocyclic amino acid AT-125 and a microbiological process for producing it are disclosed in U.S. Pat. Nos. 3,856,807 and 3,878,047. These patents also disclose the antitumor and antimicrobial properties of AT-125.

A process for the purification of AT-125 and production of certain AT-125 analogs generated during such process is disclosed in U.S. Pat. Nos. 4,225,720 and 4,232,164.

A multi-step chemical synthesis of AT-125 from 3,4-epoxycyclopentene is disclosed in U.S. Pat. No. 4,256,898 (see also U.S. Pat. No. 4,275,214). Also disclosed are novel analogs of AT-125 including the 3-bromo analog.

An attempt by Baldwin, et al. to synthesize AT-125 by a cycloaddition of chloronitrile oxide and vinyl glycine was unsuccessful (*J. Chem. Soc. Chem. Comm.*, 1976, pg. 795–796). The failure of this approach was attributed to the unreactivity of chloronitrile oxide toward cycloaddition.

Recently, Hagedorn, et al., employing Baldwin's approach, have reported a one-step synthesis of the bromo analog of AT-125, i.e.

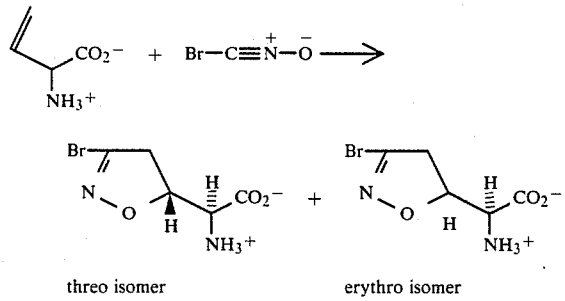

A key feature of this synthesis, described in *Tetrahedron Lett.* 21:229–230 (1980), is the use of the more reactive bromonitrile oxide in place of chloronitrile oxide used by Baldwin. A serious drawback of the Hagedorn method, however, is the production of the undesired threo isomer in approximately 75% yield and the extreme difficulty of separating the erythro and threo isomers. Hagedorn, et al. report that the bromo analog of AT-125 (the erythro isomer) has antimicrobial and antitumor properties comparable to those of AT-125.

A total synthesis of AT-125 and its C-5 epimer (threo isomer) is reported by Silverman, et al. in *J. Am. Chem. Soc.* 103:7357–7358 (1981). Synthesis of AT-125 was carried out in eight steps fom L-erythro-β-chloroglutamic acid in a 17% overall yield. The corresponding threo isomer of AT-125 was obtained in 15% overall yield from L-threo-β-chloroglutamic acid.

While threo AT-125 and the corresponding threo bromo AT-125 have been disclosed in the literature, there has been no indication that these C-5 epimers possess biological activity.

In view of the promising antitumor properties reported for AT-125 and its bromo analog, it would be desirable to have a practical commercial process for chemically synthesizing these compounds from inexpensive, readily available starting materials. Such a process would also advantageously provide both the erythro and threo isomers of these compounds in substantially pure form in high yield and with substantially fewer steps than processes previously described.

SUMMARY OF THE INVENTION

In one aspect the present invention is directed to novel chemical process for synthesizing (αS, 5S)-α-amino-3-chloro-2-isoxazoline-5-acetic acid, (αS, 5S)-α-amino-3-bromo-2-isoxazoline-5-acetic acid, (αS, 5R)-α-amino-3-chloro-2-isoxazoline-5-acetic acid and (αS, 5R)-α-amino-3-bromo-2-isoxazoline-5-acetic acid (both as racemic mixtures and optically active isomers) from an inexpensive, readily available starting material, i.e. cis-2-butene-1,4-diol.

In another aspect the present invention provides novel chemical intermediates useful in the above-described processes.

In another aspect the present invention provides a method for therapeutically treating a mammalian host affected by a malignant tumor which comprises administering to said host an effective tumor-inhibiting dose of (αS, 5R)-α-amino-3-chloro-2-isoxazoline-5-acetic acid or (αS, 5R)-α-amino-3-bromo-2-isoxazoline-5-acetic acid (either as racemic mixtures or resolved optically active isomers) or a pharmaceutically acceptable salt thereof.

In still another aspect, the present invention provides a novel and efficient process for producing vinyl glycine, a β,γ-unsaturated α-amino acid reported to be an intermediate in various enzymatic processes as well as an intermediate for the synthesis of bromo AT-125 (see Hagedorn reference cited above).

DETAILED DESCRIPTION

The present invention provides new chemical processes for preparing compounds of the formula

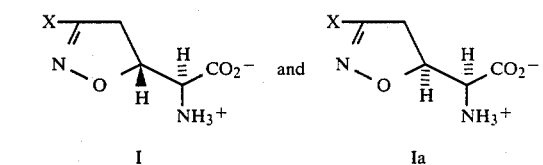

wherein X is chloro or bromo, and pharmaceutically acceptable salts thereof, from a known starting material, cis-2-butene-1,4-diol. The processes allow the above-mentioned compounds (both as dl-racemic mixtures and as resolved d- and l-optical isomers) to be produced substantially more efficiently, economically and in higher yields than heretofore possible.

One variation of the overall process for producing the compounds of formulae I and Ia wherein X is bromo is shown in the following reaction scheme:

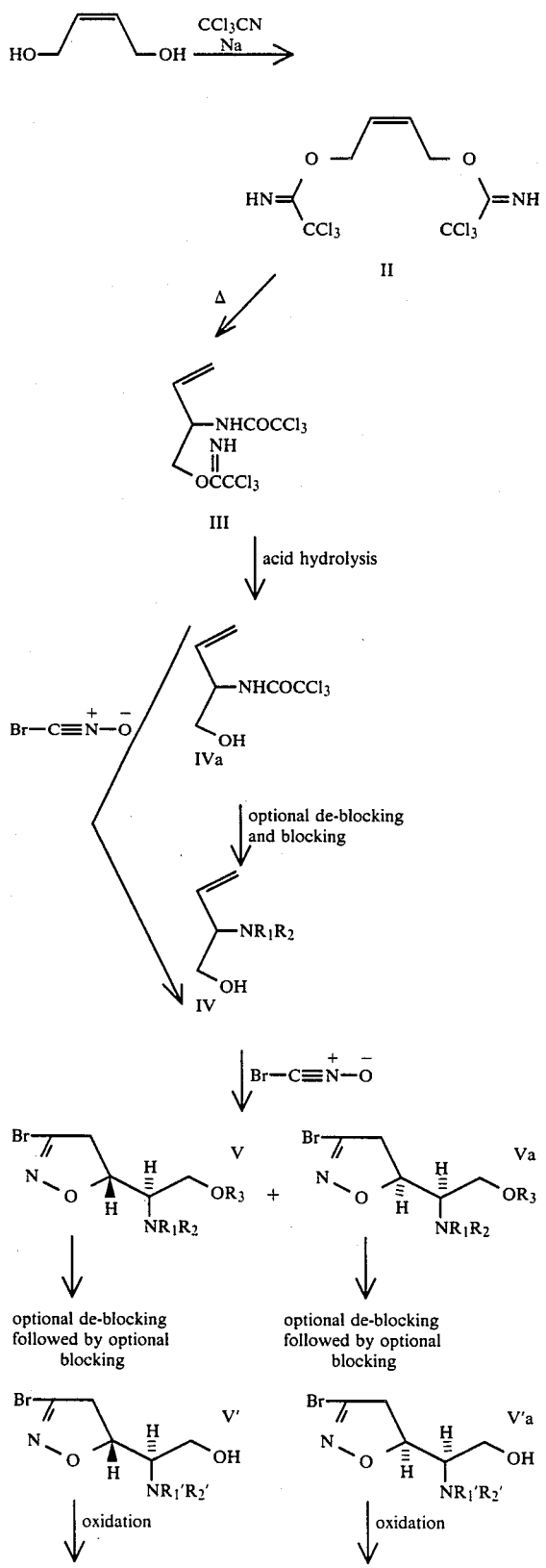

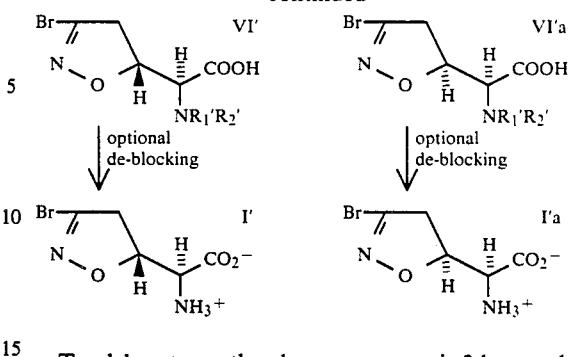

To elaborate on the above process, cis-2-butene-1,4-diol is readily converted to its bis-trichloroimidate ester (intermediate II) by treatment with trichloroacetonitrile in the presence of a catalytic amount of sodium. Most advantageously, the trichloroacetonitrile is added to a cooled ($\leq 4°$ C.) mixture of the cis-2-butene-1,4-diol and sodium and stirred at room temperature for several hours. Upon neutralization of the reaction mixture, the bis-imidate intermediate II may be recovered, e.g. by fractional distillation.

Intermediate II may then be subjected to thermal rearrangement, i.e. [3,3]sigmatropic rearrangement, by heating in the presence or absence of an inert organic solvent. For best results the rearrangement is preferably carried out at a temperature in the range of about 130°–185° C. When a solvent is to be used, inert aromatic or aliphatic hydrocarbons having a boiling point range of about 130°–185° C. are advantageously used, e.g. o-xylene, m-xylene, p-xylene, hemimellitene, pseudodocumene, mesitylene, n-propylbenzene, cumene, n-butylbenzene, isobutylbenzene, sec-butylbenzene, tert-butylbenzene, p-cymene, etc.

Intermediate III may be used directly in the cycloaddition reaction to be described below or, as indicated in the reaction scheme, it may be subjected to acid hydrolysis to produce 2-(2,2,2-trichloro-1-oxoethyl)amino-3-butene-1-ol (intermediate IVa) and a by-product of the formula

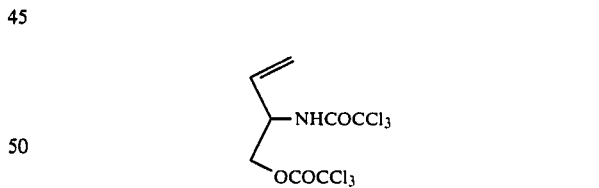

which may be readily separated as by silica gel column chromatography.

As will be apparent to those skilled in the art, the 2-(2,2,2-trichloro-1-oxoethyl)amino-3-butene-1-ol (formula IVa) is an amino-protected form of 2-amino-3-butene-1-ol, a known compound. Thus, the trichloroacetyl protecting group of intermediate IVa may, if desired, be readily removed by known methods, e.g. base hydrolysis to give 2-amino-3-butene-1-ol which in turn may be converted to another amino-protected derivative by conventional procedures.

To further elaborate, intermediate IVa may be deblocked to remove the trichloroacetyl protecting group and then converted into an amino-protected derivative of the general formula

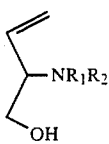

IV wherein either (a) $R_1$ is hydrogen and $R_2$ is a conventional amino-protecting group or (b) $R_1$ and $R_2$ when taken together with the nitrogen to which they are attached represent a conventional amino-protecting group. Examples of conventional amino-protecting groups are described in J. W. Barton in *Protective Groups in Organic Chemistry*, J. F. W. McOmie, Ed., Plenum Press, New York, N.Y., 1973, Chapter 2. Another good source of representative amino-protecting groups is provided by R. A. Boissonnas in *Advances in Organic Chemistry* 3:159–190 (1963). Still further examples of suitable amino-protecting groups for use in preparing intermediate IV may be found in U.S. Pat. No. 4,256,898. It will be clear to those skilled in the art that the particular amino-protecting group used is not critical and that one need only select a group stable to the subsequent steps of the reaction process, i.e. cycloaddition and oxidation, and which is removable under conditions which do not adversely affect the remainder of the amino acid end-product. Examples of such groups will be readily apparent to those skilled in the art.

Suitable amino-protecting groups for preparing intermediate IV include, for example, acyl groups such as formyl, acetyl and substituted acetyl (e.g. haolgenated acetyl), benzoyl and substituted benzoyl, alkoxycarbonyl, halogenated alkoxycarbonyl, alkenyloxycarbonyl, aralkoxycarbonyl, halogenated aralkoxycarbonyl, (lower)alkyl, benzyl and benzyl derivatives, trityl and trityl derivatives, sulfenyl derivatives, sulfonyl derivatives, diacyl derivatives such as phthalimido or succinimido or derivatives thereof and Schiff bases formed with aldehydes or ketones. Specific examples of suitable amino-protecting groups include formyl, acetyl, trifluoroacetyl, trichloroacetyl, benzoyl, benzyloxycarbonyl, 2,2,2-trichloroethoxycarbonyl, isobutyloxycarbonyl, cyclopentyloxycarbonyl, cyclohexyloxycarbonyl, 1-adamantyloxycarbonyl, 4-methoxybenzyloxycarbonyl, 4-nitrobenzyloxycarbonyl, 3,4-dimethoxycarbonyl, 4-chlorobenzyloxycarbonyl, 4-bromobenzyloxycarbonyl, allyloxycarbonyl, 4-phenylazobenzyloxycarbonyl, 4-(4-methoxyphenylazo)benzyloxycarbonyl, isopropoxycarbonyl, tertbutoxycarbonyl, 3-iodopropoxycarbonyl, 2furfuryloxycarbonyl, trimethylsilylethoxycarbonyl, 8-quinolyloxycarbonyl, benzyl, trityl, p-toluenesulfonyl, benzenesulfonyl, 2-nitrophenylsulfenyl or phenylthiocarbonyl. Divalent amino-protecting groups (i.e. $R_1$ and $R_2$ taken together in formula IV) include phthalimido, succinimido and derivatives thereof.

Intermediate IV or intermediate III is then reacted with an excess of bromonitrile oxide in an inert solvent (aqueous or organic or mixed aqueous-organic) such as water, ethyl acetate, methylene chloride, dioxane, tetrahydrofuran, acetone, chloroform or $C_1$–$C_4$ alcohols to give intermediates V and Va. This [3+2]cycloaddition reaction affords a diasteriomeric mixture of erythro and threo intermediates having the formula

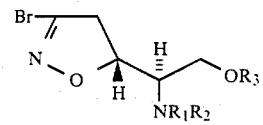

(threo)

and

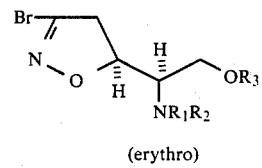

(erythro)

wherein $R_3$ is hydrogen or

which can be separated as by fractional crystallization. The bromonitrile oxide reagent is preferably generated in situ from dibromoformaldoxime as described in *Tetrahedron Letters* 21:229–230 (1980).

Intermediates V and/or Va of the formula

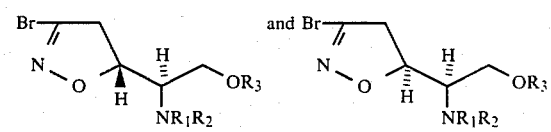

are then de-blocked by conventional procedures either to selectively remove the hydroxyl protecting group or to produce the corresponding amino alcohol(s) of the formula

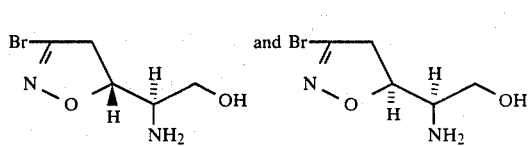

which, in turn, may, if desired, be converted by conventional procedures into intermediates of the formula

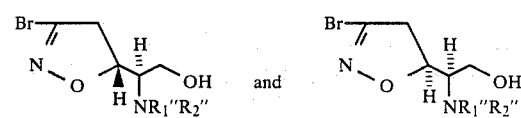

wherein either (a) $R_1''$ is hydrogen and $R_2''$ represents a conventional amino-protecting group (either the same as or different than the original $R_2$ protecting group) or (b) $R_1''$ and $R_2''$ when taken together with the nitrogen to which they are attached represent a conventional amino-protecting group (either the same as or different than the original $R_1$–$R_2$ protecting group). The optional step of de-blocking and blocking intermediates V and/or Va allows substitution of other suitable amino-protecting groups for the amino-protecting group $R_2$ or $R_1R_2$. Also, the de-blocked amino alcohol(s) can also be formed from intermediates V and Va and such alcohol(s) can be used directly in the subsequent oxidation step. In general, however, it is preferred to use an amino-protected form of intermediate V or Va in the oxidation step and then de-block the amino-protected acid to give the desired amino acid end-product.

In the procedure of the present invention, then, there is prepared from cis-2-butene-1,4-diol an intermediate of the general formula

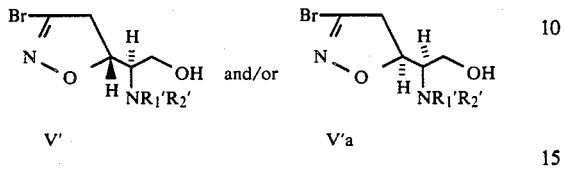

wherein either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino-protecting group. Intermediates V' and V'a, therefore, encompass intermediates V and Va in which the hydroxyl protecting group has been removed, the de-blocked amino alcohols thereof and the amino protected derivatives prepared from the amino alcohols.

The erythro and/or threo intermediates of formula V' and V'a are next subjected to oxidation to obtain intermediate VI' and VI'a of the formulae

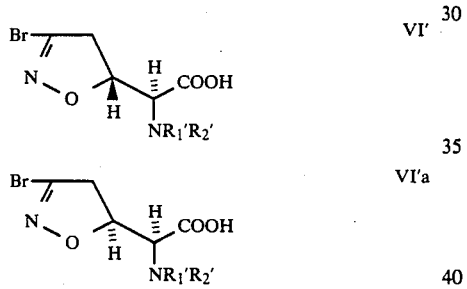

A wide variety of oxidizing agents may be used in this step including chromium (VI) compounds (e.g. chromic acid or an alkali metal chromate) manganese (VII) compounds (e.g. potassium permanganate), potassium ruthenate, potassium persulfate, ruthenium (VIII) oxide, etc. Chromic acid is an especially preferred oxidizing agent since it provides the oxidized intermediate in high yield. The oxidation step can be done either with a mixture of the erythro and threo intermediates (in which case the oxidized products will be separated following the oxidation) or, preferably, with the separated isomer V' or V'a. Generally, an inert organic solvent is employed for the oxidation step, e.g. acetone, dimethylformamide, methylene chloride, etc.

The desired amino acid end-products I' and/or I'a may be obtained when $R_1'$ and $R_2'$ are other than hydrogen by removing the amino-protecting groups from intermediate VI' and/or VI'a. Procedures for removing such protecting groups are extensively illustrated in the Barton and Boissonnas references mentioned above. In the case of the trichloroacetyl protecting group, for example, the intermediate VI' or VI'a may be subjected to alkaline hydrolysis, e.g. with aqueous $Ba(OH)_2$ or NaOH, to generate the desired zwitterionic product.

In the above-described procedure, one has the alternative of carrying out the cycloaddition reaction with either intermediate III or intermediate IV. It is preferred to use intermediate IV since this avoids co-production of an undesired by-product in the synthesis.

A preferred variation of the synthetic procedure described above is shown by the following reaction scheme:

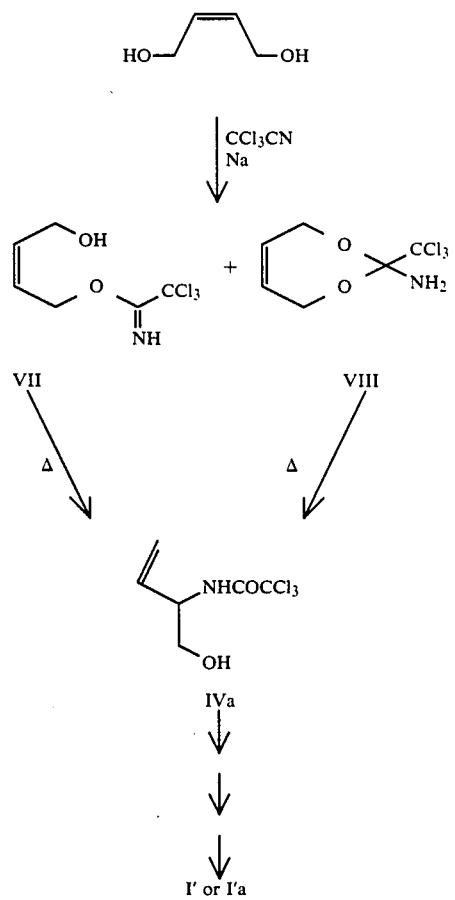

The above process variation allows the key alcohol intermediate IVa to be produced directly in high yield from either intermediate VII or VIII without co-production of an undesired by-product as in the case of the first-described reaction scheme.

To elaborate on the above variation, cis-2-butene-1,4-diol when reacted with trichloroacetonitrile and a catalytic amount of sodium was found to produce a mixture of the products

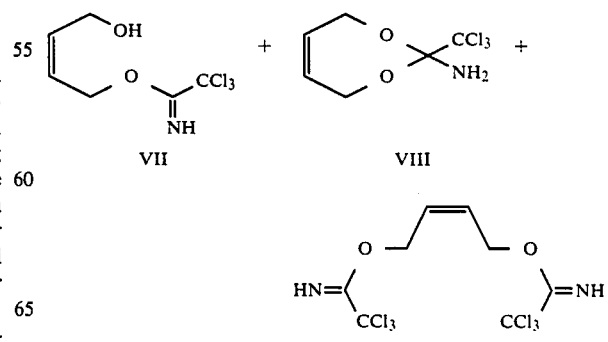

with the relative proportions of such products being dependent upon the reaction conditions and the ratio of reactants. Production of the key alcohol intermediate IVa from intermediate II requires a thermal rearrangement step to produce a trichloroimidate intermediate III (see first reaction scheme described above) and then an acid hydrolysis step which yields not only the desired alcohol IVa but also an undesired by-product of the formula

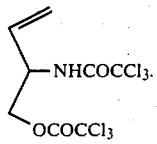

to circumvent the reduction in product (i.e. intermediate IVa) yield due to this by-product formation, it is preferred to isolate the cyclic intermediate VIII or the monoimidate intermediate VII (instead of intermediate II) and to subject either or both of these intermediates to the thermal rearrangement step as described above in connection with intermediate II. Direct rearrangement of intermediates VII and/or VIII yields the desired alcohol intermediate IVa in high yield and without the necessity of separating out from the reaction mixture an undesired by-product. Once intermediate IVa is produced, it may be reacted as in the first-described reaction scheme above to give product I' and/or I'a.

Optimum production of monoimidate intermediate VII, the most preferred of the three intermediates produced from cis-2-butene-1,4-diol, is accomplished by adding about one equivalent of trichloroacetonitrile to a solution of cis-2-butene-1,4-diol and a catalytic amount of sodium in an inert organic solvent such as tetrahydrofuran. Best results are achieved when the addition of trichloroacetonitrile is carried out with cooling, preferably at temperatures at or below about 4° and most preferably in the range of about 0° to −25° C. Under such preferred conditions, a mixture of monoimidate VII, trichloroimidate II and cyclic intermediate VIII is obtained in an approximate ratio of about 75:5:20, respectively. The desired intermediate VII or VIII, most preferably VII, may then be recovered from the reaction mixture as by fractional distillation and subjected to thermal rearrangement as discussed above to produce alcohol intermediate IVa in high purity and good yield.

In another aspect the present invention provides a novel process for preparing (αS,5S)-α-amino-3-chloro-2-isoxazoline-5-acetic acid and (αS,5R)-α-amino-3-chloro-2-isoxazoline-5-acetic acid of the formulae

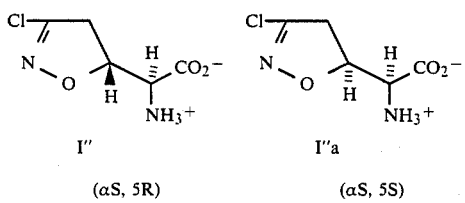

and pharmaceutically acceptable salts thereof from the intermediates of the formulae

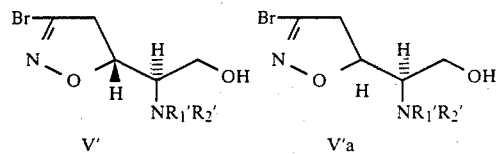

wherein either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino-protecting group. In this process, intermediate V' or V'a as prepared above from cis-2-butene-1,4-diol is reacted with hydrogen chloride or hydrochloric acid in an inert solvent such as methanol or ethyl acetate, preferably with heating and most preferably under reflux conditions, to produce respectively, the corresponding chloro intermediates of the formula

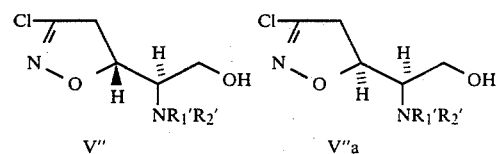

which can then be oxidized as described above in connection with intermediates V' and V'a to give the chloro acids of the formulae

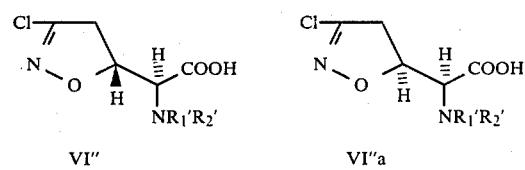

which may, if necessary, be de-protected as described above to give the desired amino acid I" and/or I"a.

In yet another aspect the present invention provides a new and efficient process for the preparation of vinyl glycine on a commercial scale. This process may be shown by the following reaction scheme:

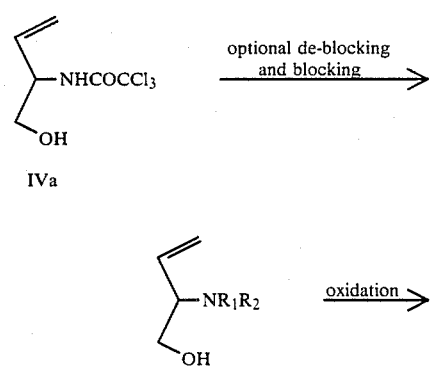

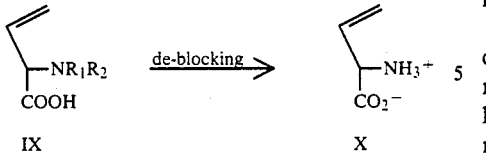

Alcohol intermediate IVa (as prepared above) is optionally converted to a different amino-protected form by removing the trichloroacetyl protecting group, e.g. by basic hydrolysis, to give 2-(2,2,2-trichloro-1-oxoethyl)amino-3-butene-1-ol, which is then reacted by methods known per se to give amino-protected intermediate IV. Intermediate IV (which now encompasses IVa) may then be oxidized as described above in connection with oxidation of intermediates V' and V'a to give amino-protected vinyl glycine of the formula IX. Removal of the amino-protecting group, e.g. by base hydrolysis in the case of the trichloroacetyl group, provides vinyl glycine in high yield.

The protected vinyl glycine produced above (intermediate IX) may be subjected to a cycloaddition reaction with bromonitrile oxide under substantially the same conditions as employed in the first-described reaction scheme to give a diasteriomer mixture of

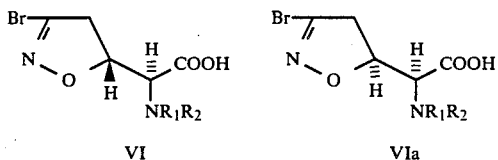

wherein either (a) $R_1$ is hydrogen and $R_2$ is a conventional amino-protecting group, or (b) $R_1$ and $R_2$ when taken together with the nitrogen to which they are attached represent a conventional amino-protecting group, from which theoretically the individual isomers VI and VIa could be separated and then de-protected to give amino acids I' and I'a, respectively. When, however, the cycloaddition reaction was attempted with intermediate IX (in the form of 2-trichloroacetamido-3-butenoic acid of the formula

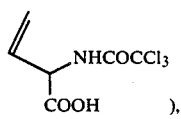

recovery of the erythro isomer (e.g. by fractional crystallization) was extremely poor. Moreover, attempts to resolve the diasteriomeric mixture by column chromatography were unsuccessful. Thus, for an efficient synthesis of intermediates VI' or VI'a, it is necessary to employ an intermediate of the formula

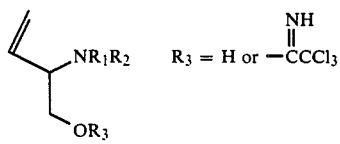

in the cycloaddition with bromonitrile oxide. Use of this intermediate results in a much more efficient and commercially feasible route for synthesis of the desired heterocyclic amino acids than heretofore achieved.

The various steps described above for preparation of compounds I', I'a, I" and I"a can either be conducted on racemic mixtures of the appropriate reactants or a resolution can be carried out at any stage along the process route and the remaining steps conducted upon optically active reactants. Resolution of the racemic mixtures can be accomplished utilizing conventional methods of resolution well-known to those skilled in the art. For example, salts can be formed with optically active acids such as D- or L-tartartic acid, the L(+)-acid, in the case of preparation of AT-125, giving the antipode which leads to AT-125 of the natural configuration. The respective salts may be obtained optically pure by recrystallization several times from a solvent such as ethanol. The amino acid end-products are preferably obtained in resolved form with the L-isomer being the most preferred biologically active form. The invention, however, emcompasses preparation of racemic forms of the end-products as well as the individual optical isomers.

Since compounds I', I'a, I" and I"a prepared by the processes of the present invention are amphoteric compounds, they form salts with acids, alkali metals (including ammonia), alkaline earth metals and amines. Suitable salts may be prepared as disclosed more fully in U.S. Pat. No. 4,256,898. The compounds may be recovered in the zwitterionic form and, if desired, converted by per se known methods to a pharmaceutically acceptable salt thereof. Also, the amino acids may be recovered in the form of salts in which case they may, if desired, be converted by per se known methods to the zwitterionic form or, if desired, further converted to a pharmaceutically acceptable salt which differs from the originally recovered salt form.

Compounds of formula V', V'a, V" and V"a wherein $R_1'$ and $R_2'$ are both hydrogen may also form salts with organic (e.g. maleic, acetic, citric, oxalic, succinic, benzoic, tartaric, lactic, fumaric, ascorbic, etc.) or inorganic (e.g. hydrochloric, hydrobromic, hydroiodic, phosphoric, sulfuric, etc.) acids and such acid addition salts (which need not be pharmaceutically acceptable since these compounds are intermediates) are included within the scope of the present invention. Similarly, other intermediates (e.g. those of formula VI', VI'a, VI" and VI"a) which contain carboxyl groups or free amino groups may form salts with bases or acids and such salts are intended to be included within the scope of the present invention.

The present invention also comprises those embodiments according to which compounds used as intermediate products are used as starting materials and the remaining steps are carried out with these, or the process is discontinued at any stage. Furthermore, starting materials can be used in the form of derivatives or can be formed during the reaction.

A preferred embodiment of the present invention comprises the process for the preparation of (αS,5S)-α-amino-3-bromo-2-isoxazoline-5-acetic acid or a pharmaceutically acceptable salt thereof, which process comprises the consecutive steps of (1) oxidizing an intermediate of the formula

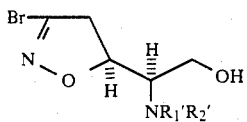

wherein either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino protecting group, to produce an intermediate of the formula

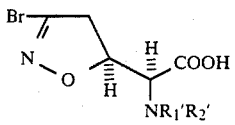

wherein $R_1'$ and $R_2'$ are as defined above; and (2) when $R_1'$ and $R_2'$ are other than hydrogen, removing the amino-protecting group of intermediate VI'a to produce the desired acid or a pharmaceutically acceptable salt thereof.

Another preferred embodiment comprises the process for the preparation of ($\alpha$S,5R)-$\alpha$-amino-3-bromo-2-isoxazoline-5-acetic acid or a pharmaceutically acceptable salt thereof, which process comprises the consecutive steps of (1) oxidizing an intermediate of the formula

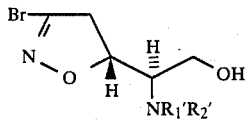

wherein either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino protecting group, to produce an intermediate of the formula

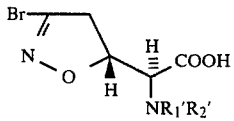

wherein $R_1'$ and $R_2'$ are as defined above; and (2) when $R_1'$ and $R_2'$ are other than hydrogen, removing the amino-protecting group of intermediate VI' to produce the desired acid or a pharmaceutically acceptable salt thereof.

Another preferred embodiment comprises the process for preparing ($\alpha$S,5S)-$\alpha$-amino-3-bromo-2-isoxazoline-5-acetic acid or a pharmaceutically acceptable salt thereof, which process comprises the steps of (1) reacting bromonitrile oxide or a precursor thereof in an inert solvent with an intermediate of the formula

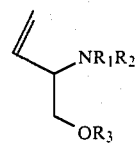

wherein $R_3$ is hydrogen or

and either (a) $R_1$ is hydrogen and $R_2$ is a conventional amino-protecting group or (b) $R_1$ and $R_2$ when taken together with the nitrogen to which they are attached represent a conventional amino-protecting group, providing that when $R_3$ is

$R_1$ is hydrogen and $R_2$ is trichloroacetyl, to produce an intermediate of the formula

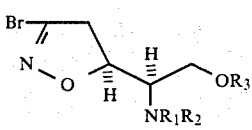

wherein $R_1$, $R_2$ and $R_3$ are as defined above;

(2) converting intermediate Va to an intermediate of the formula

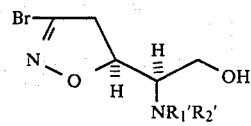

wherein either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino protecting group;

(3) oxidizing intermediate V'a to produce an intermediate of the formula

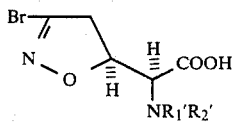

wherein $R_1'$ and $R_2'$ are as defined above; and (4) when $R_1'$ and $R_2'$ are other than hydrogen, removing the amino-protecting group of intermediate VI'a to produce the desired acid or a pharmaceutically acceptable salt thereof.

Another preferred embodiment comprises the process for preparing ($\alpha$S,5R)-$\alpha$-amino-3-bromo-2-isoxazoline-5-acetic acid or a pharmaceutically acceptable salt thereof, which process comprises the steps of (1) reacting bromonitrile oxide or a precursor thereof in an inert solvent with an intermediate of the formula

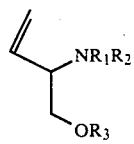

wherein $R_3$ is hydrogen or

and either (a) $R_1$ is hydrogen and $R_2$ is a conventional amino-protecting group or (b) $R_1$ and $R_2$ when taken together with the nitrogen to which they are attached represent a conventional amino-protecting group, providing that when $R_3$ is

$R_1$ is hydrogen and $R_2$ is trichloroacetyl, to produce an intermediate of the formula

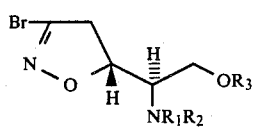

wherein $R_1$, $R_2$ and $R_3$ are as defined above;

(2) converting intermediate V to an intermediate of the formula

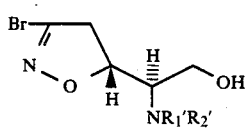

wherein either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino protecting group;

(3) oxidizing intermediate V' to produce an intermediate of the formula

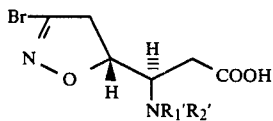

wherein $R_1'$ and $R_2'$ are as defined above; and (4) when $R_1'$ and $R_2'$ are other than hydrogen, removing the amino-protecting group of intermediate VI' to produce the desired acid or a pharmaceutically acceptable salt thereof.

Another preferred embodiment comprises the process for preparing ($\alpha$S,5S)-$\alpha$-amino-3-chloro-2-isoxazoline-5-acetic acid or a pharmaceutically acceptable salt thereof, which process comprises the steps of (1) reacting an intermediate of the formula

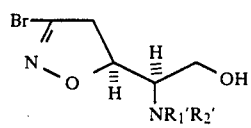

wherein either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino-protecting group, with hydrogen chloride or hydrochloric acid in an inert solvent to produce an intermediate of the formula

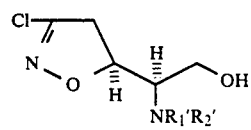

wherein $R_1'$ and $R_2'$ are defined above;

(2) oxidizing intermediate V"a to produce an intermediate of the formula

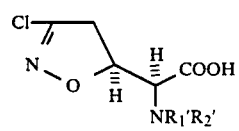

wherein $R_1'$ and $R_2'$ are as defined above; and (3) when $R_1'$ and $R_2'$ are other than hydrogen, removing the amino-protecting group of intermediate VI"a to produce the desired acid or a pharmaceutically acceptable salt thereof.

Another preferred embodiment comprises the process for preparing ($\alpha$S,5R)-$\alpha$-amino-3-chloro-2-isoxazoline-5-acetic acid or a pharmaceutically acceptable salt thereof, which process comprises the steps of (1) reacting an intermediate of the formula

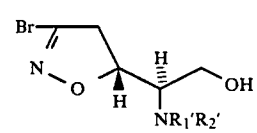

wherein either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino-protecting group, with hydrogen chloride or hydrochloric acid in an inert solvent to produce an intermediate of the formula

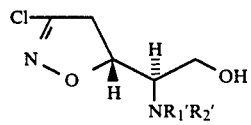

wherein $R_1'$ and $R_2'$ are as defined above;

(2) oxidizing intermediate V''' to produce an intermediate of the formula

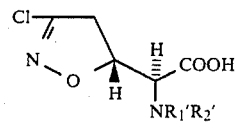 VI'' wherein $R_1'$ and $R_2'$ are as defined above; and (3) when $R_1'$ and $R_2'$ are other than hydrogen, removing the amino-protecting group of intermediate VI'' to produce the desired acid or a pharmaceutically acceptable salt thereof.

Another preferred embodiment comprises the process for preparing vinyl glycine which process comprises the steps of (1) oxidizing an intermediate of the formula

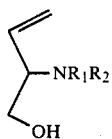 IV wherein either (a) $R_1$ is hydrogen and $R_2$ is a conventional amino-protecting group or (b) $R_1$ and $R_2$ when taken together with the nitrogen to which they are attached represent a conventional amino-protecting group, to produce an intermediate of the formula

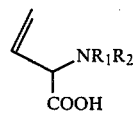 IX wherein $R_1$ and $R_2$ are as defined above; and (2) removing the amino-protecting group of intermediate IX to produce the desired vinyl glycine product.

Another preferred embodiment comprises the process for preparing intermediate IVa, which process comprises the steps of (1) subjecting an intermediate of the formula

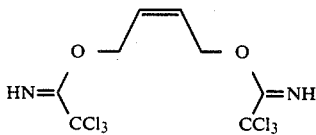 II to thermal rearrangement to produce in intermediate of the formula

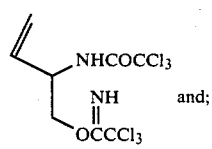 III (2) subjecting intermediate III to acid hydrolysis to produce the desired product.

Another preferred embodiment comprises the process for preparing intermediate IVa, which process comprises subjecting to thermal rearrangement an intermediate of the formula

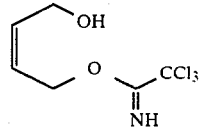 VII or

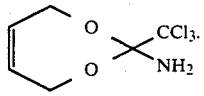 VIII

Another preferred embodiment comprises the process for preparing intermediate II, intermediate VII or intermediate VIII, which process comprises reacting cis-2-butene-1,4-diol with trichloroacetonitrile in the presence of a catalytic amount of sodium and, subsequently, isolating the desired intermediate from the reaction mixture.

A still further preferred embodiment comprises the process for preparing intermediate IV, which process comprises the steps of (1) removing the trichloroacetyl protecting group from an intermediate of the formula

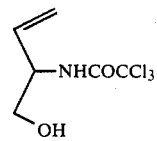 IVa to produce an intermediate of the formula

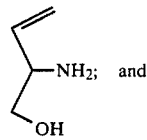

(2) converting the so-produced intermediate to the corresponding amino-protected intermediate of formula IV.

With respect to the various novel intermediates produced according to the processes of the present invention, preferred embodiments may be represented by the following formulae:

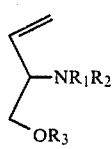 (1)

wherein $R_3$ is hydrogen or

and either (a) $R_1$ is hydrogen and $R_2$ is a conventional amino-protecting group or (b) $R_1$ and $R_2$ taken together with the nitrogen to which they are attached represent a conventional amino-protecting group, providing that when $R_3$ is

$R_1$ is hydrogen and $R_2$ is trichloroacetyl;

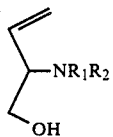  (2)

wherein either (a) $R_1$ is hydrogen and $R_2$ is formyl, acetyl, trifluoroacetyl, trichloroacetyl, benzoyl, benzyloxycarbonyl, 2,2,2-trichloroethoxycarbonyl, isobutyloxycarbonyl, cyclopentyloxycarbonyl, cyclohexyloxycarbonyl, 1-adamantyloxycarbonyl, 4-methoxybenzyloxycarbonyl, 4-nitrobenzyloxycarbonyl, 3,4-dimethoxycarbonyl, 4-chlorobenzyloxycarbonyl, 4-bromobenzyloxycarbonyl, allyloxycarbonyl, 4-phenylazobenzyloxycarbonyl, 4-(4-methoxyphenylazo)benzyloxycarbonyl, isopropoxycarbonyl, tert-butoxycarbonyl; 3-iodopropoxycarbonyl, 2-furfuryloxycarbonyl, trimethylsilylethoxycarbonyl, 8-quinolyloxycarbonyl, benzyl, trityl, p-toluenesulfonyl, benzenesulfonyl, 2-nitrophenylsulfenyl or phenylthiocarbonyl, or (b) $R_1$ and $R_2$ taken together with the nitrogen to which they are attached represent a phthalimido or succinimido group;

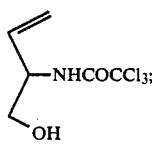  (3)

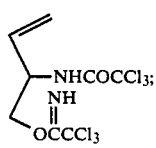  (4)

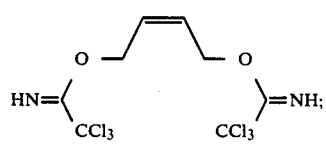  (5)

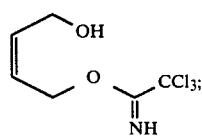  (6)

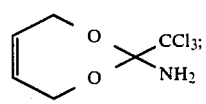  (7)

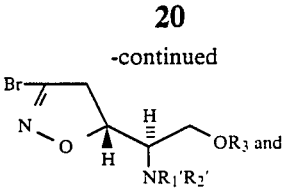  (8)

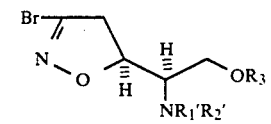

wherein $R_3$ is hydrogen or

and either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino-protecting group, providing that when $R_3$ is

$R_1'$ is hydrogen and $R_2'$ is trichloroacetyl, or an acid addition salt thereof when $R_1'$ and $R_2'$ are both hydrogen;

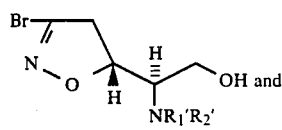  (9)

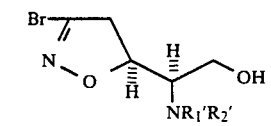

wherein either (a) $R_1'$ is hydrogen and $R_2'$ is formyl, acetyl, trifluoroacetyl, trichloroacetyl, benzoyl, benzyloxycarbonyl, 2,2,2-trichloroethoxycarbonyl, isobutyloxycarbonyl, cyclopentyloxycarbonyl, cyclohexyloxycarbonyl, 1-adamantyloxycarbonyl, 4-methoxybenzyloxycarbonyl, 4-nitrobenzyloxycarbonyl, 3,4-dimethoxycarbonyl, 4-chlorobenzyloxycarbonyl, 4-bromobenzyloxycarbonyl, allyloxycarbonyl, 4-phenylazobenzyloxycarbonyl, 4-(4-methoxyphenylazo)benzyloxycarbonyl, isopropoxycarbonyl, tert-butoxycarbonyl, 3-iodopropoxycarbonyl, 2-furfuryloxycarbonyl, trimethylsilylethoxycarbonyl, 8-quinolyloxycarbonyl, benzyl, trityl, p-toluenesulfonyl, benzenesulfonyl, 2-nitrophenylsulfenyl or phenylthiocarbonyl, or (b) $R_1'$ and $R_2'$ taken together with the nitrogen to which they are attached represent a phthalimido or succinimido group;

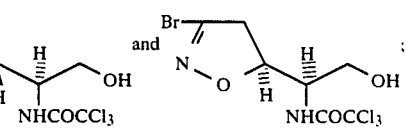  (10)

-continued

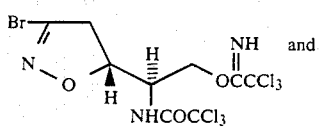(11)

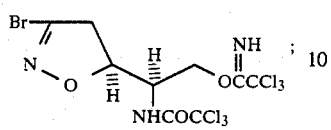

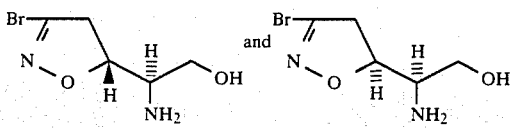(12)

or an acid addition salt thereof;

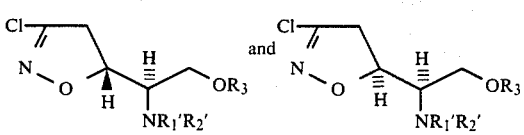(13)

wherein R$_3$ is hydrogen or $$-\underset{\underset{\text{CCl}_3}{\|}}{\overset{\text{NH}}{\text{C}}}$$

and either (a) R$_1'$ and R$_2'$ are both hydrogen, (b) R$_1'$ is hydrogen and R$_2'$ is a conventional amino-protecting group or (c) R$_1'$ and R$_2'$ when taken together with the nitrogen to which they are attached represent a conventional amino-protecting group, providing that when R$_3$ is $$-\underset{\underset{\text{CCl}_3}{\|}}{\overset{\text{NH}}{\text{C}}},$$

R$_1'$ is hydrogen and R$_2'$ is trichloroacetyl; or an acid addition salt thereof when R$_1'$ and R$_2'$ are both hydrogen;

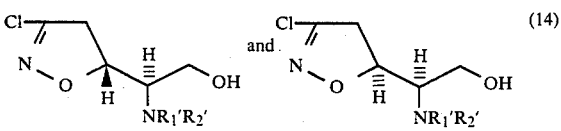(14)

wherein either (a) R$_1'$ is hydrogen and R$_2'$ is formyl, acetyl, trifluoroacetyl, trichloroacetyl, benzoyl, benzyloxycarbonyl, 2,2,2-trichloroethoxycarbonyl, isobutyloxycarbonyl, cyclopentyloxycarbonyl, cyclohexyloxycarbonyl, 1-adamantyloxycarbonyl, 4-methoxybenzyloxycarbonyl, 4-nitrobenzyloxycarbonyl, 3,4-dimethoxycarbonyl, 4-chlorobenzyloxycarbonyl, 4-bromobenzyloxycarbonyl, allyloxycarbonyl, 4-phenylazobenzyloxycarbonyl, 4-(4-methoxyphenylazo)benzyloxycarbonyl, isopropoxycarbonyl, tert-butoxycarbonyl, 3-iodopropoxycarbonyl, 2-furfuryloxycarbonyl, trimethylsilylethoxycarbonyl, 8-quinolyloxycarbonyl, benzyl, trityl, p-toluenesulfonyl, benzenesulfonyl, 2-nitrophenylsulfenyl or phenylthiocarbonyl, or (b) R$_1'$ and R$_2'$ when taken together with the nitrogen to which they are attached represent a phthalimido or succinimido group;

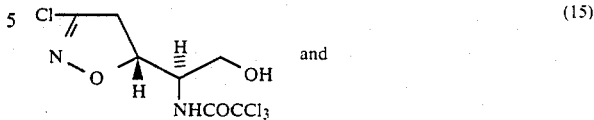(15)

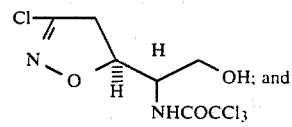

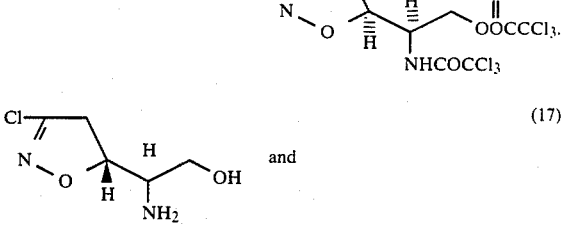(16)

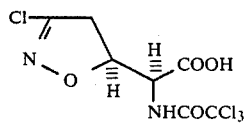(17)

an acid addition salt thereof.

As mentioned above (αS,5S)-α-amino-3-chloro-2-isoxazoline-5-acetic acid (AT-125) and (αS,5S)-α-amino-3-bromo-2-isoxazoline-5-acetic acid (and pharmaceutically acceptable salts thereof) have been disclosed as having antimicrobial and antitumor activity. While the corresponding threo isomers of these compounds have been disclosed in the prior art, there has been no indication that these isomers possess biological activity. The present inventors have unexpectedly found that the threo isomers of AT-125 and its bromo analog possess significant antitumor activity and may, therefore, be used in the treatment of malignant tumors in mammals.

Additionally, the present inventors have unexpectedly discovered that dl-erythro-2-(2,2,2-trichloro-1-oxoethyl)amino-3-chloro-4,5-dihydro-5-isoxazoleacetic acid of the formula

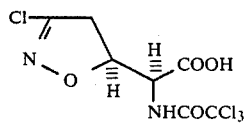

and dl-erythro-2-(2,2,2-trichloro-1-oxoethyl)amino-3-bromo-4,5-dihydro-5-isoxazoleacetic acid of the formula

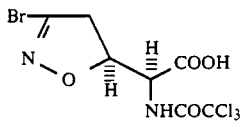

possess significant antitumor activity per se and may thus be used not only as intermediates for preparing AT-125 and bromo AT-125 but also as antitumor agents for the treatment of malignant tumors in mammals.

To illustrate the antitumor activity of the above-described threo isomers and N-protected amino acids, ($\alpha$S,5R)-$\alpha$-amino-3-bromo-2-isoxazoline-5-acetic acid, dl-erythro-2-(2,2,2-trichloro-1-oxoethyl)amino-3-chloro-4,5-dihydro-5-isoxazoleacetic acid and dl-erythro-2-(2,2,2-trichloro-1-oxoethyl)amino-3-bromo-4,5-dihydro-5-isoxazoleactic acid were tested for antitumor activity against the transplantable mouse tumor, L-1210 leukemia. Results are shown in the tables below. The methodology used generally followed the protocols of the National Cancer Institute [see, for example, *Cancer Chemotherapy Rep.*, Part 3, 3:1–103 (1972)]. The essential experimental details are given at the bottom of the tables.

Effect of ($\alpha$S, 5R)-$\alpha$-Amino-3-Bromo-2-Isoxazoline-5-Acetic Acid on Mouse L-1210 Leukemia

| Material | Dose, IP mg/kg/inj | MST Days | Effect MST % T/C | AWC, gm d.5 | Survivors Day 5(30) |
|---|---|---|---|---|---|
| AT-125 | 4 | 12.0 | 200 | −3.0 | 6/6 |
| | 2 | 10.0 | 167 | −1.7 | 6/6 |
| Compound of Example 16 (in H$_2$O) | 32 | 9.0 | 150 | −0.3 | 6/6 |
| | 16 | 8.0 | 133 | +1.5 | 6/6 |
| | 8 | 8.0 | 133 | +0.6 | 6/6 |
| | 4 | 7.0 | 117 | −0.1 | 6/6 |
| | 2 | 6.5 | 108 | +1.4 | 6/6 |
| | 1 | 6.5 | 108 | +0.9 | 6/6 |
| Control | Saline | 6.0 | — | +1.4 | 9/9 |

Tumor inoculum: 10$^6$ ascites cells implanted i.p.
Host: CDF$_1$ ♀ mice.
Tox: <4/6 mice alive on Day 5.
Treatment: qd 1→5.
Evaluation: MST = median survival time.
Effect: % T/C = (MST treated/MST control) × 100.
Criteria: % T/C ≧ 125 considered significant antitumor activity.

Effect of dl-Erythro-2-(2,2,2-Trichloro-1-oxoethyl)amino-3-chloro-4,5-dihydro-5-isoxazoleacetic Acid on Mouse L-1210 Leukemia

| Material | Dose, IP mg/kg/inj | MST Days | Effect MST % T/C | AWC, gm d.5 | Survivors Day 5(30) |
|---|---|---|---|---|---|
| AT-125 | 8 | 12.5 | 192 | −3.0 | 6/6 |
| | 4 | 10.5 | 162 | −3.3 | 6/6 |
| | 2 | 11.0 | 169 | −0.1 | 5/5 |
| | 1 | 10.0 | 154 | −0.1 | 6/6 |
| Compound of Ex. 9 | 16 | 10.0 | 154 | −1.3 | 3/4 |
| | 8 | 10.0 | 154 | +1.5 | 4/4 |
| | 4 | 8.0 | 123 | +1.0 | 4/4 |
| | 2 | 7.0 | 108 | +0.3 | 4/4 |
| | 1 | 7.0 | 108 | +0.5 | 3/3 |
| | 0.5 | 7.0 | 108 | +0.3 | 4/4 |

-continued
Effect of dl-Erythro-2-(2,2,2-Trichloro-1-oxoethyl)amino-3-chloro-4,5-dihydro-5-isoxazoleacetic Acid on Mouse L-1210 Leukemia

| Material | Dose, IP mg/kg/inj | MST Days | Effect MST % T/C | AWC, gm d.5 | Survivors Day 5(30) |
|---|---|---|---|---|---|
| Control | Saline | 6.5 | — | +2.0 | 10/10 |

Tumor inoculum: 10$^6$ ascites cells implanted i.p.
Host: CDF$_1$ ♀ mice
Treatment: QD 1→5
Tox: <3/4 mice alive on Day 5
Evaluation: MST = median survival time
Effect: % T/C = (MST treated/MST control) × 100
Criteria: % T/C ≧ 125 considered significant antitumor activity Effect of dl-Erythro-2-(2,2,2-Trichloro-1-oxoethyl)amino-3-bromo-4,5-dihydro-5-isoxazoleacetic Acid on Mouse L-1210 Leukemia

| Treatment Material | Dose, IP Schedule | MST mg/kg/inj | Days | Effect MST % T/C | AWC, gm d.5 | Survivors Day 5(30) |
|---|---|---|---|---|---|---|
| AT-125 | gd 1→5 | 2 | 9.0 | 150 | −0.7 | 6/6 |
| | | 1 | 8.0 | 133 | +0.1 | 6/6 |
| Compound of Ex. 6 | gd 1→5 | 64 | 8.5 | 142 | −0.3 | 4/4 |
| | | 32 | 7.0 | 117 | +1.9 | 5/5 |
| | | 16 | 8.0 | 133 | −0.3 | 4/4 |
| | | 8 | 7.0 | 117 | +1.5 | 4/4 |
| | | 4 | 7.0 | 117 | +1.6 | 4/4 |
| | | 2 | 6.5 | 108 | +1.5 | 4/4 |
| Control | Saline | | 6.0 | — | +2.0 | 8/10 |

Tumor inoculum: 10$^6$ ascites cells implanted i.p.
Host: CDF$_1$ ♀ mice
Evaluation: MST = median survival time
Effect: % T/C = (MST treated/MST control) × 100
Criteria: % T/C ≧ 125 considered significant antitumor activity In yet another aspect of the invention, a pharmaceutical composition is provided which comprises an effective tumor-inhibiting amount of ($\alpha$S,5R)-$\alpha$-amino-3-bromo-2-isoxazoline-5-acetic acid, ($\alpha$S,5R)-$\alpha$-amino-3-chloro-2-isoxazoline-5-acetic acid, dl-erythro-2-(2,2,2-trichloro-1-oxoethyl)amino-3-chloro-4,5-dihydro-5-isoxazoleacetic acid or dl-erythro-2-(2,2,2-trichloro-1-oxoethyl)amino-3-bromo-4,5-dihydro-5-isoxazoleacetic acid, or a pharmaceutically acceptable salt thereof, in combination with an inert pharmaceutically acceptable carrier or diluent. These compositions may be made up in any appropriate pharmaceutical form by conventional procedures.

For use as antitumor agents in mammals, the threo amino acid isomers and the erythro N-protected amino acids may be administered substantially as described in U.S. Pat. No. 4,256,898 for the erythro AT-125 derivatives disclosed therein. It will be appreciated that the actual preferred dosages of the compounds will vary according to the particular compound being used, the particular composition formulated, the mode of administration and the particular situs, host and disease being treated. Many factors that modify the action of the drugs will be taken into account by those skilled in the art, e.g. age, body weight, sex, diet, time of administration, rate of excretion, condition of the host, drug combinations, reaction sensitivities and severity of the disease. Optimal dosages for a given set of conditions can be ascertained by those skilled in the art using conventional dosage determination tests in view of the experimental animal data provided, the available data on AT-125 and the above-mentioned guidelines.

The following examples are provided to illustrate the present invention and are note intended to be limiting on the scope thereof. All temperatures are in degrees Centigrade. Melting points given below were recorded on a Thomas-Hoover Capillary melting point apparatus and are uncorrected. $^1$H NMR spectra were recorded on a Varian XL 100 or Perkin Elmer R 12B (60 MHz) spectrometer in CDCl$_3$ unless otherwise stated. IR spectra were obtained with a Beckman Model 4240 spectrophotometer and the IR figures are $\nu_{max}$ in cm$^{-1}$. UV-visible spectra were recorded on a Varian-Cary-219 spectrophotometer. Thin layer chromatography (TLC) was carried out on 0.25 mm E. Merck precoated silica gel plates (60F-254) using UV light and/or iodine vapors as visualizing agent. Flash chromatography (J. Org. Chem. 14: 2923, 1978) was performed using Silica Woelm (32-63 mm). Solvents were evaporated under reduced pressure and below 50° C.

PREPARATION OF STARTING MATERIALS

Preparation 1:

Glyoxylic Acid Oxime

HCCOH.H$_2$O
||
NOH

To glyoxylic acid hydrate (10 g) in water (50 ml) was added hydroxylamine hydrochloride (9.4 g, 0.135 mmoles). The reaction mixture was stirred at room temperature for 6 hours and then extracted with diethyl ether (3×50 ml). The combined organic extract was dried (Na$_2$SO$_4$) and evaporated to afford a white solid (9 g). Crystallization from diethyl ether-Skellysolve B (tradename of Skelly Oil Co. for petroleum solvent comprising isomeric hexanes and having a b.p. of 60°-68° C.) afforded the title product as colorless needles. m.p. 62°-70°. IR (KBr): 2600-3600, 1710, 1625 and 1020 cm$^{-1}$.

Anal. Calc'd for C$_2$H$_3$NO$_3$.H$_2$O: C, 22.43; H, 4.67; N, 13.08. Found: C, 22.24; H, 4.30; N, 13.49.

Preparation 2:

Dibromoformaldoxime

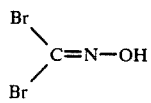

To glyoxylic acid oxime hydrate (12 g, 112 mmoles) in water (60 ml) was added under stirring and ice bath temperature (0°-4° C.), methylene chloride (130 ml) and sodium bicarbonate (18.83 g, 224 mmoles). To this two phase mixture was added bromine (35.84 g, 448 mmoles) in methylene chloride (50 ml), and stirring was continued for 7 hours (at 0° C.) followed by additional stirring at room temperature for 13 hours. Excess of bromine was destroyed by careful addition of solid sodium thiosulfate. The organic layer was separated and the aqueous layer further extracted with methylene chloride (2×100 ml). The combined organic extracts were dried (Na$_2$SO$_4$) and evaporated to afford the title product as a white solid (11.4 g, 50.13% yield). A portion of this material was recrystallized from Skellysolve B to obtain an analytical sample. m.p. 65°-68°. IR (KBr): 3000-3600, 1580 and 980 cm$^{-1}$.

Anal. Calc'd for CHNOBr$_2$: C, 5.91; H, 0.49; N, 6.90. Found: C, 5.40; H, 0.20; N, 6.95.

EXAMPLE 1 dl-2-(2,2,2-Trichloro-1-oxoethyl)amino-3-butene-1-ol

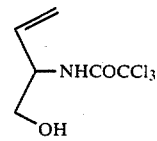

A. cis-2-Butene-1,4-diol-1,4-bistrichloroimidate

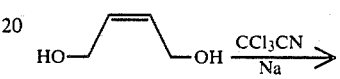

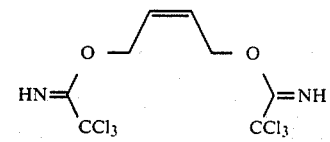

To cis-2-butene-1,4-diol (3.7 g, 42 mmoles) containing ~10 mg Na there was added dropwise trichloroacetonitrile (13.68 g, 92.3 mmoles) at ~0°-4°. The solution was then stirred at room temperature for 24 hours. After neutralization with 3 drops of glacial acetic acid, the reaction mixture was subjected to vacuum distillation. A major fraction distilling at 133°-138° (0.2 mm Hg) was characterized as the bis-imidate title product (8.74 g, 55%). IR (CDCl$_3$): 3350, 1675, 805 and 835 cm$^{-1}$. $^1$H NMR was consistent with the structure indicated above.

Anal. Calc'd for C$_8$H$_8$N$_2$O$_2$Cl$_6$: C, 25.50; H, 2.14; N, 7.43; Cl, 56.44. Found: C, 25.31; H, 2.17; N, 7.66; Cl, 58.96.

B. dl-2,2,2-Trichloroethanimidic acid, α-[(2,2,2-trichloro-1-oxoethyl)amino]-3-butenyl ester

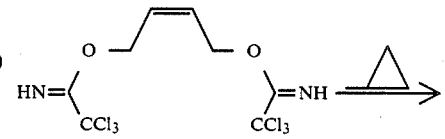

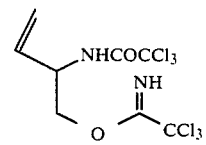

A sample of the bis-imidate product prepared in Example 1A (8.47 g, 22.45 mmoles) was heated on an oil bath at 180°-185° for 1 hour under continuous stirring. The resulting black syrup was taken up into 50 ml of diethyl ether and decolorized to an orange solution with charcoal treatment. Concentration of this solution afforded the title product as a thick orange syrup (7.1 g, 83.8%), the $^1$H NMR of which suggested it to be in a fairly pure state. A portion of this sample was chromatographed on silica gel (20 g) and eluted with Skellysolve B/methylene chloride (1:3). The title compound was isolated as a white solid which, upon recrystallization from diethyl ether/Skellysolve B, afforded colorless crystals. m.p. 71.5°–73°. IR (KBr): 3450–3420, 1685, 1670, 1535, 800 and 835 cm$^{-1}$. $^1$H NMR was consistent with the structure indicated above.

Anal. Calc'd for $C_8H_8N_2O_2Cl_6$: C, 25.50; H, 2.14; N, 7.43; Cl, 56.44. Found: C, 25.48; H, 1.93; N, 7.48; Cl, 56.53.

C. dl-2-(2,2,2-Trichloro-1-oxoethyl)amino-3-butene-1-ol

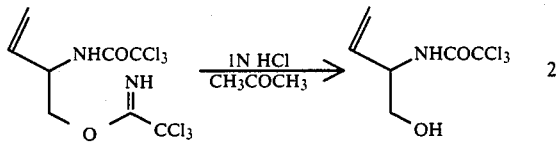

To the trichloroimidate product of Example 1B (4.0 g, 10.61 mmoles) dissolved in acetone (100 ml) there was added 1N HCl (5 ml). The reaction mixture was then stirred at ~0° for 1 hour. The precipitates formed were filtered off and the filtrate was concentrated to a solid residue. This residue was extracted with methylene chloride (100 ml) and the extract concentrated to a syrup. TLC (methylene chloride) of the syrup revealed the presence of two components ($R_f$'s ~0.7 and 0.15) in addition to a trace amount of starting material ($R_f$=0.6). Column chromatography on silica gel (74 g) using gradient elution with 2:1 (v/v) methylene chloride/Skellysolve B (500 ml), methylene chloride (500 ml), 1% methanol in methylene chloride (500 ml) and 2% methanol in methylene chloride (300 ml) afforded the two components.

The faster moving component ($R_f$~0.7) was identified as 2-trichloroacetamido-3-butene-1-ol-1-trichloroacetate (706 mg, 17%). m.p. 105.5°–107°. IR (KBr): 3300, 1760, 1695 and 1535 cm$^{-}$. $^1$H NMR was consistent with the structure

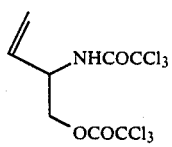

Anal. Calc'd for $C_8H_7NO_3Cl_6$: C, 25.43; H, 1.87; N, 3.71; Cl, 56.29. Found: C, 25.84; H, 1.94; N, 3.92; Cl, 56.05.

The slower moving component ($R_f$~0.15) was identified as 2-trichloroacetamido-3-butene-1-ol (1.3 g, 53%). IR (KBr): 3420, 1700, 1520 and 820 cm$^{-1}$. $^1$H NMR data was consistent with the structure indicated above for the title product.

EXAMPLE 2 dl-Threo-2,2,2-trichloroethanimidic acid, 2-(3-bromo-4,5-dihydro-5-isoxazolyl)-2-[2,2,2-trichloro-1-oxoethyl)-amino] ethyl ester and dl-Erythro-2,2,2-trichloroethanimidic acid, 2-(3-bromo-4,5-dihydro-5-isoxazolyl)-2-[2,2,2-trichloro-1-oxoethyl)amino]ethyl ester

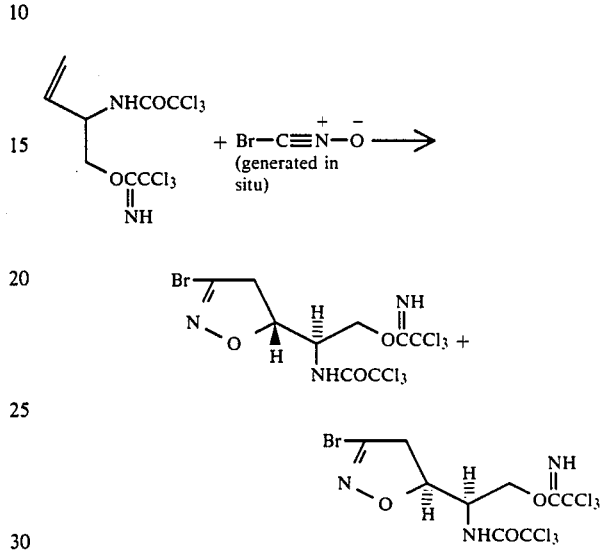

To 2-(2,2,2-trichloro-1-oxoethyl)amino-3-butene-1-ol-trichloroimidate (700 mg, 1.81 mmole) in methylene chloride (10 ml) there were added in sequence dibromoformaldoxime (1.13 g, 5.57 mmole), potassium bicarbonate (931 mg, 9.30 mmoles) and 3 drops of water. The suspension was stirred at room temperature for 2 hours at which time TLC (ethanol/chloroform 1:10 v/v) revealed that all of the starting material was consumed. Insoluble solids were filtered off and the filtrate dried ($Na_2SO_4$) and evaporated to a yellow syrup (1.37 g). Fractional crystallization in ethyl acetate/Skellysolve B (1:4 v/v) afforded the threo title product (270 mg., 29.9%) as a white crystalline solid. m.p. 135°–136.5° IR (KBr); 3310, 3320, 1700, 1670, 1540 and 820 cm$^{-1}$. $^1$H NMR was consistent with the structure of the threo title product indicated above.

Anal. Calc'd for $C_9H_8N_3O_3Cl_6Br$: C, 21.64; H, 1.60; N, 8.42; Halogen equivalent=7. Found: C, 20.36; H, 1.64; N, 8.52; Halogen equivalent=6.7.

Flash chromatography (ethyl acetate/Skellysolve B 1:4 v/v) of the syrup contained from the above mother liquor afforded a syrup (500 mg) which upon trituration with Skellysolve B afforded a white solid (400 mg, 44.3%) of analytical purity. IR (KBr): 3400, 3340, 1705, 1670, 1515 and 820 cm$^{-1}$. $^1$H NMR was consistent with a 2:1 mixture of the threo and erythro title products.

Anal. Calc'd for $C_9H_8N_3Cl_6Br$: C, 21.64; H, 1.60; N, 8.42; Halogen equivalent=7. Found: C, 21.63; H, 1.52; N, 8.49; Halogen equivalent=7.1.

EXAMPLE 3 dl-2-(2,2,2-Trichloro-1-oxoethyl)amino-3-butenoic acid
(Protected Vinyl Glycine)

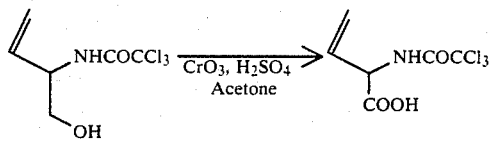

To dl-2-(2,2,2-trichloro-1-oxoethyl)amino-3-butene-1-ol (800 mg, 3.44 mmole) dissolved in acetone (50 ml) there was added chromic acid solution (prepared according to Org. Synthesis 45: 28, 1964) dropwise until an orange color persisted for ~20 minutes. The green precipitate was filtered off and the filtrate was brought to pH ~8–9 with saturated aqeuous sodium bicarbonate solution. After removal of acetone, the aqueous solution was extracted with methylene chloride (40 ml) (evaporation of which afforded starting material (169 mg) and acidified (pH 2) with 2N HCl. Extraction with diethyl ether (4×20 ml), drying of the combined extract over anhydrous $Na_2SO_4$, and evaporation of the ether afforded an oil (503 mg, 75.2%). Column chromatography (5% methanol in $CH_2Cl_2$) of a small portion of the above oil afforded the title product as a white crystalline solid (250 mg, 37.4%). m.p. 84°–87°. IR (KBr): 3320, 2800, 3400, 1725, 1690, 1520, 830 and 835 cm$^{-1}$. $^1$H NMR was consistent with the structure indicated above.

Anal. Calc'd for $C_6H_6NO_3Cl_3$: C, 29.24; H, 2.45; N, 5.68; Cl, 43.15. Found: C, 29.43; H, 2.52; N, 5.75; Cl, 41.76.

EXAMPLE 4 dl-Threo-N—[1-(3-bromo-4,5-dihydro-5-isoxazolyl)-2-hydroxyethyl]-2,2,2-trichloroacetamide and dl-Erythro-N—[1-(3-bromo-4,5-dihydro-5-isoxazolyl)-2-hydroxyethyl]-2,2,2-trichloroacetamide

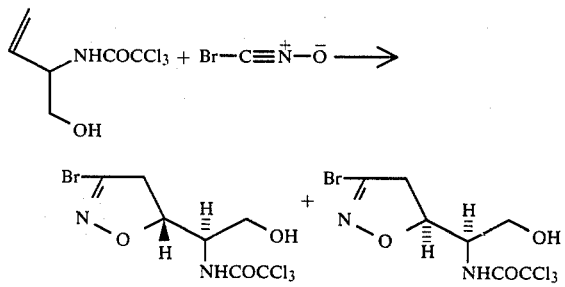

To dl-2-(2,2,2-trichloro-1-oxoethyl)amino-3-butene-1-ol (3.8 g, 16.3 mmole) dissolved in ethyl acetate (100 ml) there was added water (5 ml) and potassium carbonate (16 g, 160 mmole). To this suspension bromoformaldoxime (10 g, 49.3 mmole) was added in small portions with vigorous stirring over a period of 40 minutes. After an additional stirring for 1 hour at room temperature, the mixture was diluted with water (25 ml) and the organic layer separated. The aqueous fraction was further extracted with ethyl acetate (2×30 ml) and the combined organic extract dried ($Na_2SO_4$) and evaporated. The resulting semicrystalline solid was triturated with methylene chloride (45 ml). The insoluble crystalline material was collected (1.62 g, 28%) and characterized as the threo title product. m.p. 164°–165°. IR (KBr): 3500, 3230, 1700, 1540 and 830 cm$^{-1}$. $^1$H NMR (DMSO d$_6$) was consistent with the structure indicated above.

Anal. Calc'd for $C_7H_8N_2O_3Cl_3Br$: C, 23.72; H, 2.28; N, 7.90; Halogen equivalent=4. Found: C, 23.66; H, 2.20; N, 8.12; Halogen equivalent=4.4.

The methylene chloride-soluble fraction upon chromatography (1% methanol in methylene chloride, 1000 ml) on silica gel (70 g) afforded the erythro title product (940 mg, 16.2%) as an oil, with a trace contamination from the above-described threo isomer. The elemental analysis, IR and $^1$H NMR spectral data were consistent with the structure of the erythro isomer product indicated above.

EXAMPLE 5 dl-Threo-2-(2,2,2-trichloro-1-oxoethyl)amino-3-bromo-4,5-dihydro-5-isoxazoleacetic acid

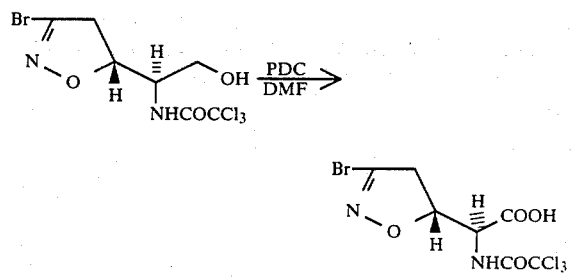

To dl-threo-N-[1-(3-bromo-4,5-dihydro-5-isoxazolyl)-2-hydroxyethyl]-2,2,2-trichloroacetamide (250 mg, 0.73 mmole) dissolved in dry dimethylformamide (2 ml) there was added pyridiniumdichromate (961 mg, 2.56 mmole; J. Org. Chem. 14: 2923, 1978) and the solution was stirred at room temperature for 18 hours. Upon dilution with water (20 ml), the mixture was partitioned between water and diethyl ether. The combined ether extract was dried ($Na_2SO_4$), passed through anhydrous $MgSO_4$ and evaporated to yield a colorless syrup (175 mg). This syrup was further purified by flash chromatography (chloroform/ethanol 10:1 v/v) followed by basic-acidic acid workup of the resulting product (as described above in connection with the product of Example 3) to yield the title product as a white crystalline solid (68 mg, 26%). m.p. 115°–120°. IR (KBr): 3280, 2600–3600, 1730, 1690, 1520, 820 and 835 cm$^{-1}$. $^1$H NMR was consistent with the structure indicated above.

Anal. Calc'd for $C_7H_6N_2O_4Cl_3Br$: C, 22.80, H, 1.63; N, 7.60; Halogen equivalent=4. Found: C, 23.18; H, 1.81; N, 7.67; Halogen equivalent=3.91.

EXAMPLE 6 dl-Erythro-α-(2,2,2-trichloro-1-oxoethyl)amino-3-bromo-4,5-dihydro-5-isoxazole acetic acid

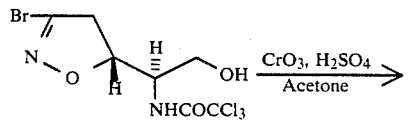

-continued
dl-Erythro-α-(2,2,2-trichloro-1-oxoethyl)amino-3-bromo-4,5-dihydro-5-isoxazole acetic acid

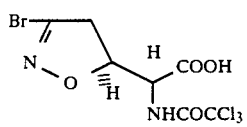

To a 1:2 mixture of dl-erythro and dl-threo-N-[1-(3-bromo-4,5-dihydro-5-isoxazolyl)-2-hydroxyethyl]-2,2,2-trichloroacetamide (3.5 g, 10.72 mmole) dissolved in acetone (50 ml) there was added chromic acid dropwise with stirring and at room temperature. Addition continued until a persistent orange coloration was obtained. The solution was brought to pH~8-9 with aqueous NaHCO$_3$ solution, concentrated (to remove acetone) and extracted with methylene chloride (2×25 ml). This methylene chloride extract upon drying and concentration afforded starting material (1.9 g). The aqueous basic solution was acidified (pH=2) and exhaustively extracted with diethyl ether. The combined ether extract was dried (Na$_2$SO$_4$) and evaporated to a syrup (1.5 g, 75% based on recovery of starting material) which, upon dissolution in chloroform (10 ml), afforded the title product as a crystalline material (400 mg, 31.5%). m.p. 155°-157°. IR (KBr): 3370, 3150, 1750, 1735, 1690, 1680, 1525 and 825 cm$^{-1}$. The $^1$H NMR (DMSO d$_6$) was consistent with the structure indicated above. No attempt was made to resolve the mother liquor.

Anal. Calc'd for C$_7$H$_6$N$_2$O$_4$Cl$_3$Br: C, 22.80; H, 1.63; N, 7.60; Halogen equivalent=4. Found: C, 22.41; H, 1.65; N, 7.62; Halogen equivalent=3.9.

EXAMPLE 7 dl-Erythro-α-amino-3-bromo-4,5-dihydro-5-isoxazoleacetic acid

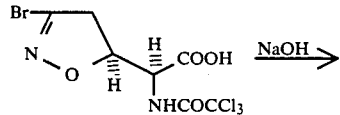

To dl-erythro-2-(2,2,2-trichloro-1-oxoethyl)amino-3-bromo-4,5-dihydro-5-isoxazoleacetic acid (100 mg, 0.27 mmole) dissolved in a 1:1 (v/v) absolute ethanol:water mixture (4 ml) there was added 10% sodium hydroxide solution (0.4 ml). The resulting solution was kept at room temperature for 24 hours. The solution was then brought to pH ~6.7 with dropwise addition of 1N HCl and the resulting solution concentrated to a solid residue. Crystallization from aqueous methanol afforded the title product (20 mg, 33%) as an amorphous solid. IR (KBr): 2600-3200 and 1010 cm$^{-1}$. $^1$H NMR (D$_2$O) was consistent with the above-identified structure. λmax(H$_2$O)=214 nm.

Anal. Calc'd for C$_5$H$_7$N$_2$O$_3$Br: C, 26.91; H, 3.14; N, 12.56. Found: C, 26.42; H, 3.07; N, 12.29.

EXAMPLE 8 dl-Erythro-N—[1-(3-chloro-4,5-dihydro-5-isoxazolyl)-2-hydroxyethyl]-2,2,2-trichloroacetamide

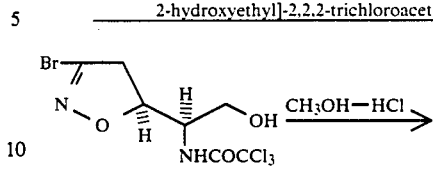

To dl-erythro-N-[1-(3-bromo-4,5-dihydro-5-isoxazolyl)-2-hydroxyethyl]-2,2,2-trichloroacetamide (5.0 g, 14.1 mmoles) dissolved in methanol (40 ml) there was added methanol (40 ml) containing acetyl chloride (10 ml). The solution was refluxed for 1 hour. Evaporation of methanol under reduced pressure afforded a yellowish syrup which was taken up into methylene chloride (50 ml). This solution upon washing with aqueous saturated sodium bicarbonate (3×20 ml) and water (1×20 ml), followed by drying (Na$_2$SO$_4$) and solvent evaporation, afforded a syrup (3.40 g). TLC (3% CH$_3$OH in CH$_2$Cl$_2$) revealed the presence of two components with Rf's 0.2 (major) and 0.1 (minor). The major component (Rf=0.2), isolated as a syrup (1.97 g, 45%) by flash chromatography on silica gel (40 g) using 1.5 liters of 1% CH$_3$OH in CH$_2$Cl$_2$ as eluant, was characterized as the title product. IR (KBr): 3200-3500, 2960, 1700-1740, 1520 and 830 cm$^{-1}$. $^1$H NMR was consistent with the indicated structure.

Anal. Calc'd for C$_7$H$_8$N$_2$O$_3$Cl$_4$: C, 27.10; H, 2.58; N, 9.03; Cl, 45.81. Found: C, 26.87; H, 2.65; N, 8.93; Cl, 44.77.

EXAMPLE 9 dl-Erythro-2-(2,2,2-trichloro-1-oxoethyl)amino-3-chloro-4,5-dihydro-5-isoxazoleacetic acid

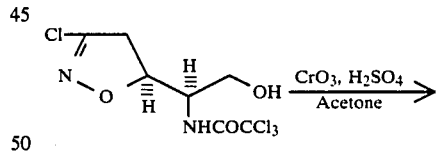

To dl-erythro-N-[1-(3-chloro-4,5-dihydro-5-isoxazolyl)-2-hydroxyethyl]-2,2,2-trichloroacetamide (1.6 g, 5.16 mmole) dissolved in acetone (50 ml) there was added with stirring at room temperature ~1 ml portions of chromic acid solution (3.5 ml). After stirring for 3.5 hours the reaction was terminated by adding a few drops of isopropyl alcohol to destroy excess chromic acid. The solution was brought to basic pH (~8-9) with aqueous sodium bicarbonate solution and filtered. The clear filtrate was concentrated and extracted with methylene chloride (3×20 ml). The aqueous layer was acidified to pH ~2 with concentrated HCl and extracted with ethyl acetate (8×30 ml). The combined ethyl acetate extract was dried (Na₂SO₄) and evaporated to yield the title compound as a light orange solid (1.61 g). Crystallization from ethyl acetate and Skellysolve B afforded the title product as a white crystalline solid (1.32 g, two crops, 79%). m.p. 154°-155°. IR (KBr): 3370, 3150, 1740, 1680, 1525 and 823 cm⁻¹. ¹H NMR was consistent with the indicated structure.

Anal. Calc'd for C₇H₆N₂O₄Cl₄: C, 25.93; H, 1.85; N, 8.64; Cl, 43.83. Found: C, 25.10; H, 1.71; N, 8.61; Cl, 44.69.

EXAMPLE 10 dl-Erythro-α-amino-3-chloro-4,5-dihydro-5-isoxazoleacetic acid

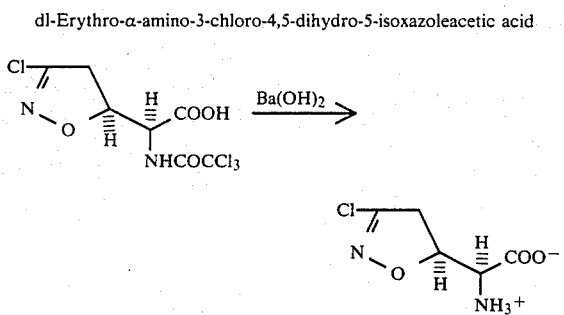

To a suspension of dl-erythro-2-(2,2,2-trichloro-1-oxyethyl)amino-3-chloro-4,5-dihydro-5-isoxazoleacetic acid (0.5 g, 1.54 mmole) in water (20 ml) there was added barium hydroxide (1.84 g, 6.16 mmole) at 45° C. with stirring. After 15 minutes, the solution was cooled and acidified with 4.5N H₂SO₄ so that the supernatant gave a negative barium test. Barium sulfate was filtered off and Amberlite IR-45 (OH⁻) (95 ml) was added to the filtrate. This reaction mixture was allowed to stand for 2 hours after which the resin was poured onto a sintered funnel and washed with water (2×50 ml). The resin was then eluted with 1N acetic acid (4×50 ml) and the combined acetic acid fraction was then lyophilized to yield the title product as an amorphous light powder (182 mg, 66%). An analytical sample was obtained by crystallization from water and sec-butanol as a crystalline solid (75 mg). IR (KBr): 2600-3200, 1600, 1630 and 1400 cm⁻¹. ¹H NMR was consistent with the indicated structure. λmax (H₂O)=216.

Anal. Calc'd for C₅H₇N₂O₃Cl: C, 33.61; H, 3.92; N, 15.69; Cl, 19.89. Found: C, 32.90; H, 3.77; N, 15.65; Cl, 18.59.

EXAMPLE 11 cis-2-Butene-1,4-diol-monotrichloroimidate

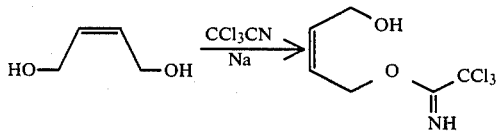

To cis-2-butene-1,4-diol (3.2 g, 35 mmole) dissolved in tetrahydrofuran (5 ml) there was added sodium (~3-5 mg) with stirring. To this solution cooled to −23° (CCl₄-dry ice bath) there was slowly added trichloroacetonitrile (5.3 g, 35 mmole) over a 15 minute period and the solution was then stirred for an additional 3 hours at −23°. The solution was kept in the cold room (~4° C.) overnight, followed by removal of the tetrahydrofuran under reduced pressure. The residual oil was subjected to distillation at ~0.2-0.3 mm Hg.

The major fraction (4.77 g, 58%) collected between 88°-102° was identified as the monotrichloroimidate title product. IR (CDCl₃): 3610, 3340, 1667, 1100 and 810 cm⁻¹. ¹H NMR was consistent with the indicated structure.

Anal. Calc'd for C₆H₈NO₂Cl₃: C, 31.00; H, 3.45; N, 6.02; Cl, 45.75. Found: C, 31.60; H, 3.66; N, 6.05; Cl, 45.06.

EXAMPLE 12

2-Amino-2-trichloromethyl 1,3-Dioxa-cyclohept-5-ene

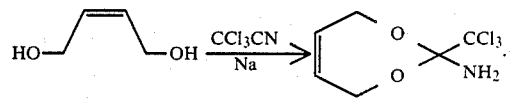

To cis-2-butene-1,4-diol (22.28 g, 252.9 mmole) there was added a catalytic amount of sodium followed by a slow addition at ~0° C. of trichloroacetonitrile (110 g, 3 equivalents). Upon completion of the trichloroacetonitrile addition, the solution was stirred at room temperature for 16 hours. The solution was acidified with 1 ml glacial acetic acid and stirred for 15 minutes. The resulting solution was distilled under reduced pressure (0.25 mm Hg) and several fractions were collected at different temperatures. The minor fraction (9.71 g) collected between 98°-110° was characterized as the cyclic title product. IR (KBr): 3430-3350, 3040, 2940-2920, 1607, 1110 and 825 cm⁻¹. ¹H NMR was consistent with the indicated structure.

Anal. Calc'd for C₆H₈NO₂Cl₃: C, 31.00; H, 3.47; N, 6.02; Cl, 45.75. Found: C, 30.90; H, 3.38; N, 6.24; Cl, 46.95.

The major fraction (~60 g) distilling at ~120°-138° was identified as cis-2-butene-1,4-diol-1,4-bistrichloroimidate.

EXAMPLE 13 dl-2-(2,2,2-Trichloro-1-oxoethyl)amino-3-butene-1-ol

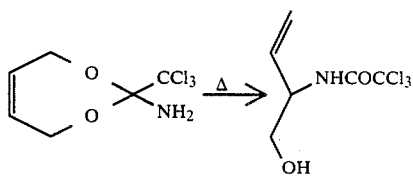

A sample of 2-amino-2-trichloromethyl 1,3-dioxacyclohept-5-ene (362 mg) in tert-butylbenzene (2 ml) was heated in an oil bath at 180°-183° for 1.5 hours. The resulting dark mixture was chromatographed on silica gel (2-3 g) using Skellysolve B as the eluant. After all tert-butylbenzene was removed, the column was eluted with methylene chloride (15 ml) followed by ethyl acetate (10 ml). Evaporation of the combined organic fractions afforded the crude rearranged title product (392 mg). Further purification by flash chromatography on silica gel (12 g) using 1% methanol in methylene chloride (300 ml) as eluant afforded a fairly pure sample of title product whose ¹H NMR spectrum was identical to that of the previously prepared sample of product prepared according to Example 1C.

EXAMPLE 14 dl-2-(2,2,2-Trichloro-1-oxoethyl)amino-3-butene-1-ol

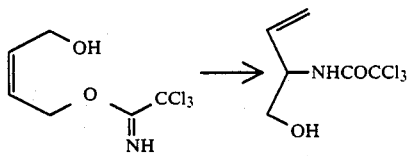

cis-2-Butene-1,4-diol-monotrichloroimidate (32 g) in tert-butylbenzene (55 ml) was refluxed at 175°–180° for 50 minutes. The mixture was cooled to room temperature and chromatographed on a silica gel (45 g) column using Skellysolve B as the eluting solvent. After the tert-butylbenzene was eluted, as evidenced by TLC (CH$_2$Cl$_2$), the column was eluted with methylene chloride. Pooling of the appropriate fractions, followed by evaporation of methylene chloride (~800 ml) afforded an oil (21.1 g, 66%) which, upon standing and drying, solidified. The $^1$H NMR spectrum of this solid was identical to that of the title product prepared as described above in Example 1C.

EXAMPLE 15

Dibromoformaldoxime

In a three-neck 12 liter flask equipped with a mechanical stirrer and a thermometer there was introduced 1000 g of a 50% solution of glyoxylic acid hydrate. The solution was then diluted with water to 3300 ml. Hydroxylamine hydrochloride (470 g) was added to this solution and the resulting solution stirred at room temperature for 24 hours. Sodium bicarbonate (1176 g) was added continuously followed by methylene chloride (5000 ml). To this well-stirred mixture at 6° C. there was added bromine (482 ml in 2500 ml CH$_2$Cl$_2$) at such a rate that the temperature of the reaction mixture did not rise above 7°–8°. After the addition was complete, stirring was continued for 3 hours with ice cooling (the bromine color disappeared ~15 minutes after the completion of the addition). The organic layer was separated and the aqueous layer reextracted with methylene chloride (5000 ml). The combined extracts were dried over anhydrous MgSO$_4$ and the solvent evaporated. The resulting residue upon crystallization from Skellysolve B (3300 ml) afforded the title product (4530 g) as a white crystalline solid. The mother liquor upon concentration afforded an additional crop of 59 g.

EXAMPLE 16 dl-Threo-α-Amino-3-bromo-4,5-dihydro-5-isoxazoleacetic acid

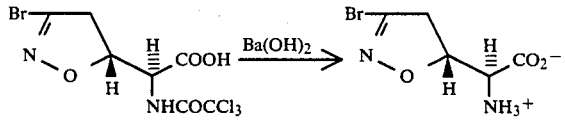

To dl-threo-2-(2,2,2-trichloro-1-oxoethyl)amino-3-bromo-4,5-dihydro-5-isoxazoleacetic acid (3.953 g, 10.7 mmole) dissolved in water (100 ml) there was added Ba(OH)$_2$ (10.15 g, 32.2 mmole) and the solution was stirred for 30 minutes at 45° C. Excess Ba(OH)$_2$ was filtered off and the resulting filtrate was acidified (pH=1) with 4.5N H$_2$SO$_4$ to ensure that all barium ions were precipitated as barium sulfate. The suspension was cooled at 0° C. for 20 minutes and then filtered with the aid of Celite. The yellowish filtrate was concentrated to ~35 ml volume and brought to pH=4.5 by adding saturated sodium bicarbonate solution. Concomitantly, the title product precipitated out of solution and was collected as a white solid (1.85 g, 77.3%). An analytical sample (mp. 193°–195°) was obtained by crystallization from hot water. The spectral data (NMR, IR) were consistent with the indicated structure.

Anal. Calc'd for C$_5$H$_7$N$_2$O$_3$Br: C, 26.93; H, 3.16; N, 12.56; Br, 35.83. Found: C, 26.95; H, 2.88; N, 12.76; Br, 35.49.

EXAMPLE 17 dl-Threo-N—[1-(3-chloro-4,5-dihydro-5-isoxazolyl)-2-hydroxyethyl)-2,2,2-trichloroacetamide

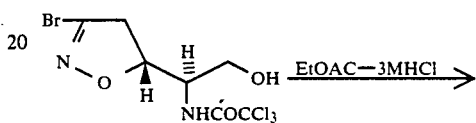

To dl-threo-N-[1-(3-bromo-4,5-dihydro-5-isoxazolyl)-2-hydroxyethyl]-2,2,2-trichloroacetamide (0.2 g, 0.56 mmoles) dissolved in ethyl acetate (5 ml) there was added hydrochloric acid (3 molar, 5 ml). The solution was refluxed for 1 hour followed by concentration of the solution to ~5 ml volume under reduced pressure. This concentrate was extracted with diethyl ether (4×25 ml). The combined extract was dried (Na$_2$SO$_4$) and evaporated to a syrup (180 mg) which, upon crystallization from ethyl acetate and Skellsolve B, afforded the title compound as white crystals (100 mg, 57%); m.p. ~138°–140° C. The spectral date (IR, $^1$H NMR) was consistent with the indicated structure.

Anal. Calc'd for C$_7$H$_8$N$_2$O$_3$Cl$_4$: C, 27.10; H, 2.58; N, 9.03; Cl, 45.81. Found: C, 27.46; H, 2.73; N, 8.89; Cl, 44.96.

EXAMPLE 18 dl-Threo-2-(2,2,2-trichloro-1-oxoethyl)amino-3-chloro-4,5-dihydro-5-isoxazoleacetic acid

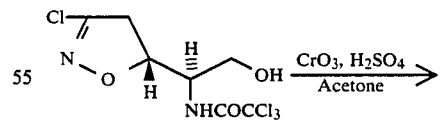

If in the general procedure of Example 9 the dl-erythro-N-[1-(3-chloro-4,5-dihydro-5-isoxazolyl)-2-hydroxyethyl]-2,2,2-trichloroacetamide used therein is replaced by an equimolar amount of dl-threo-N-[1-(3-chloro-4,5-dihydro-5-isoxazolyl)-2-hydroxyethyl]-

2,2,2-trichloroacetamide, there is produced the title product.

EXAMPLE 19 dl-Threo-α-Amino-3-chloro-4,5-dihydro-5-isoxazoleacetic acid

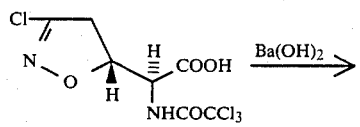

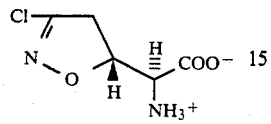

If in the general procedure of Example 10 the dl-erythro-2-(2,2,2-trichloro-1-oxyethyl)amino-3-amino-3-chloro-4,5-dihydro-5-isoxazoleacetic acid used therein is replaced by an equimolar amount of dl-threo-2-(2,2,2-trichloro-1-oxyethyl)amino-3-chloro-4,5-dihydro-5-isoxazoleacetic acid, there is produced the title product.

We claim:

1. An intermediate of the formula

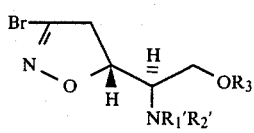

wherein $R_3$ is hydrogen or

and either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino-protecting group, providing that when $R_3$ is

$R_1'$ is hydrogen and $R_2'$ is trichloroacetyl, or an acid addition salt thereof when $R_1'$ and $R_2'$ are both hydrogen.

2. An intermediate of claim 1 wherein either (a) $R_1'$ is hydrogen and $R_2'$ is formyl, acetyl, trifluoroacetyl, trichloroacetyl, benzoyl, benzyloxycarbonyl, 2,2,2-trichloroethoxycarbonyl, isobutyloxycarbonyl, cyclopentyloxycarbonyl, cyclohexyloxycarbonyl, 1-adamantyloxycarbonyl, 4-methoxybenzyloxycarbonyl, 4-nitrobenzyloxycarbonyl, 3,4-dimethoxycarbonyl, 4-chlorobenzyloxycarbonyl, 4-bromobenzyloxycarbonyl, allyloxycarbonyl, 4-phenylazobenzyloxycarbonyl, 4-(4-methoxyphenylazo)benzyloxycarbonyl, isopropoxycarbonyl, tertbutoxycarbonyl, 3-iodopropoxycarbonyl, 2-furfuryloxycarbonyl, trimethylsilylethoxycarbonyl, 8-quinolyloxycarbonyl, benzyl, trityl, p-toluenesulfonyl, benzenesulfonyl, 2-nitrophenylsulfenyl or phenylthiocarbonyl, or (b) $R_1'$ and $R_2'$ taken together with the nitrogen to which they are attached represent a phthalimido or succinimido group.

3. The intermediate of claim 1 wherein $R_1'$ is hydrogen, $R_2'$ is trichloroacetyl and $R_3$ is hydrogen.

4. The intermediate of claim 1 wherein $R_1'$ is hydrogen, $R_2'$ is

5. The intermediate of claim 1 having the formula

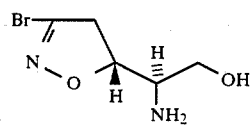

or an acid addition salt thereof.

6. An intermediate of the formula

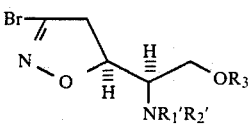

wherein $R_3$ is hydrogen or

and either (a) $R_1'$ and $R_2'$ are both hydrogen, (b) $R_1'$ is hydrogen and $R_2'$ is a conventional amino-protecting group of (C) $R_1'$ and $R_2'$ when taken together with the nitrogen to which they are attached represent a conventional amino-protecting group, providing that when $R_3$ is

$R_1'$ is hydrogen and $R_2'$ is trichloroacetyl, or an acid addition salt thereof when $R_1'$ and $R_2'$ are both hydrogen.

7. An intermediate of claim 6 wherein either (a) $R_1'$ is hydrogen and $R_2'$ is formyl, acetyl, trifluoroacetyl, trichloroacetyl, benzoyl, benzyloxycarbonyl, 2,2,2-trichloroethoxycarbonyl, isobutyloxycarbonyl, cyclopentyloxycarbonyl, cyclohexyloxycarbonyl, 1-adamantyloxycarbonyl, 4-methoxybenzyloxycarbonyl, 4-nitrobenzyloxycarbonyl, 3,4-dimethoxycarbonyl, 4-chlorobenzyloxycarbonyl, 4-bromobenzyloxycarbonyl, allyloxycarbonyl, 4-phenylazobenzyloxycarbonyl, 4-(4-methoxyphenylazo)benzyloxycarbonyl, isopropoxycarbonyl, tertbutoxycarbonyl, 3-iodopropoxycarbonyl, 2-furfuryloxycarbonyl, trimethylsilylethoxycarbonyl, 8-quinolyloxycarbonyl, benzyl, trityl, p-toluenesulfonyl, benzenesulfonyl, 2-nitrophenylsulfenyl or phenylthiocarbonyl, or (b) $R_1'$ and $R_2'$ taken together with the nitrogen to which they are attached represent a phthalimido or succinimido group.

8. The intermediate of claim 6 wherein $R_1'$ is hydrogen, $R_2'$ is trichloroacetyl and $R_3$ is hydrogen.

9. The intermediate of claim 6 wherein $R_1'$ is hydrogen, $R_2'$ is trichloroacetyl and $R_3$ is

10. The intermediate of claim 6 having the formula

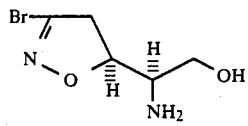

or an acid addition salt thereof.

11. An intermediate of the formula

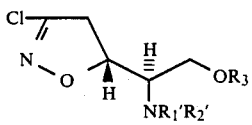

wherein $R_3$ is hydrogen or

and either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino-protecting group, providing that when $R_3$ is

$R_1'$ is hydrogen and $R_2'$ is trichloroacetyl, or an acid addition salt thereof when $R_1'$ and $R_2'$ are both hydrogen.

12. An intermediate of claim 11 wherein either (a) $R_1'$ is hydrogen and $R_2'$ is formyl, acetyl, trifluoroacetyl, trichloroacetyl, benzoyl, benzyloxycarbonyl, 2,2,2-trichloroethoxycarbonyl, isobutyloxycarbonyl, cyclopentyloxycarbonyl, cyclohexyloxycarbonyl, 1-adamantyloxycarbonyl, 4-methoxybenzyloxycarbonyl, 4-nitrobenzyloxycarbonyl, 3,4-dimethoxycarbonyl, 4-chlorobenzyloxycarbonyl, 4-bromobenzyloxycarbonyl, allyloxycarbonyl, 4-phenylazobenzyloxycarbonyl, 4-(4-methoxyphenylazo)benzyloxycarbonyl, isopropoxycarbonyl, tertbutoxycarbonyl, 3-iodopropoxycarbonyl, 2-furfuryloxycarbonyl, trimethylsilylethoxycarbonyl, 8-quinolyloxycarbonyl, benzyl, trityl, p-toluenesulfonyl, benzenesulfonyl, 2-nitrophenylsulfenyl or phenylthiocarbonyl, or (b) $R_1'$ and $R_2'$ taken together with the nitrogen to which they are attached represent a phthalimido or succinimido group.

13. The intermediate of claim 11 wherein $R_1'$ is hydrogen, $R_2'$ is trichloroacetyl and $R_3$ is hydrogen.

14. The intermediate of claim 11 wherein $R_1'$ is hydrogen, $R_2'$ is trichloroacetyl and $R_3$ is

15. The intermediate of claim 11 having the formula

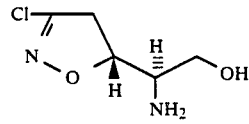

or an acid addition salt thereof.

16. An intermediate of the formula

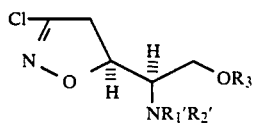

wherein $R_3$ is hydrogen or

and either (a) $R_1'$ and $R_2'$ are both hydrogen, (b) $R_1'$ is hydrogen and $R_2'$ is a conventional amino-protecting group or (c) $R_1'$ and $R_2'$ when taken together with the nitrogen to which they are attached represent a conventional amino-protecting group, providing that when $R_3$ is

$R_1'$ is hydrogen and $R_2'$ is trichloroacetyl, or an acid addition salt thereof when $R_1'$ and $R_2'$ are both hydrogen.

17. An intermediate of claim 16 wherein either (a) $R_1'$ is hydrogen and $R_2'$ is formyl, acetyl, trifluoroacetyl, trichloroacetyl, benzoyl, benzyloxycarbonyl, 2,2,2-trichloroethoxycarbonyl, isobutyloxycarbonyl, cyclopentyloxycarbonyl, cyclohexyloxycarbonyl, 1-adamantyloxycarbonyl, 4-methoxybenzyloxycarbonyl, 4-nitrobenzyloxycarbonyl, 3,4-dimethoxycarbonyl, 4-chlorobenzyloxycarbonyl, 4-bromobenzyloxycarbonyl, allyloxycarbonyl, 4-phenylazobenzyloxycarbonyl, 4-(4-methoxyphenylazo)benzyloxycarbonyl, isopropoxycarbonyl, tertbutoxycarbonyl, 3,iodopropoxycarbonyl, 2-furfuryloxycarbonyl, trimethylsilyethoxycarbonyl, 8-quinolyloxycarbonyl, benzyl, trityl, p-toluenesulfonyl, benzenesulfonyl, 2-nitrophenylsulfenyl or phenylthiocarbonyl, or (b) $R_1'$ and $R_2'$ taken together with the nitrogen to which they are attached represent a phthalimido or succinimido group.

18. The intermediate of claim 16 wherein $R_1'$ is hydrogen, $R_2'$ is trichloroacetyl and $R_3$ is hydrogen.

19. The intermediate of claim 16 wherein $R_1'$ is hydrogen, $R_2'$ is trichloroacetyl and $R_3$ is

20. The intermediate of claim 16 having the formula
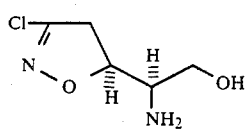
or an acid addition salt thereof.
21. The intermediate of the formula
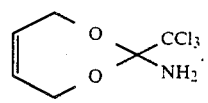
* * * * *